United States Patent [19]
Connolly et al.

[11] Patent Number: 5,925,769
[45] Date of Patent: Jul. 20, 1999

[54] ACETYLENIC 1,5-DIARYLPYRAZOLES AS ANTIINFLAMMATORY AGENTS

[75] Inventors: Peter Connolly, New Providence; Michael Wachter, Bloomsbury; Robert Chen, Belle Mead, all of N.J.

[73] Assignee: Ortho Pharmaceutical, Corp., Raritan, N.J.

[21] Appl. No.: 09/139,239

[22] Filed: Aug. 25, 1998

Related U.S. Application Data

[60] Provisional application No. 60/058,295, Sep. 9, 1997.

[51] Int. Cl.$^6$ .................. A61K 31/415; A61K 31/47; C07D 231/12; C07D 401/12
[52] U.S. Cl. .................. 548/375.1; 514/406; 544/140; 544/363; 544/371; 546/175; 546/211; 546/275.4; 548/365.7
[58] Field of Search .................. 548/365.7, 375.1; 546/175, 233.4; 514/406

[56] References Cited

U.S. PATENT DOCUMENTS

| | | |
|---|---|---|
| 5,288,751 | 2/1994 | Brooks et al. . |
| 5,506,261 | 4/1996 | Brooks et al. . |
| 5,516,789 | 5/1996 | Brooks et al. . |
| 5,559,144 | 9/1996 | Brooks et al. . |
| 5,616,596 | 4/1997 | Basha et al. . |
| 5,681,966 | 10/1997 | Cai et al. . |

OTHER PUBLICATIONS

Scifinder Alkynyll Hydroxyurea Search Results Aug. 20, 1998.

*Primary Examiner*—Robert W. Ramsuer
*Attorney, Agent, or Firm*—Kenneth J. Dow

[57] ABSTRACT

Compounds of Formula I

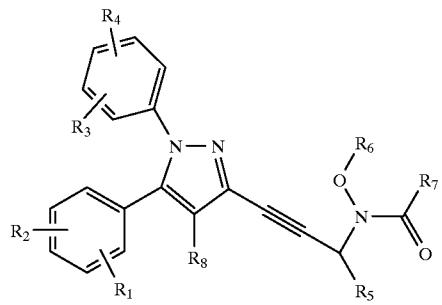

wherein, $R_1$ through $R_7$ are described herein. These compounds inhibit the production of arachidonic acid products associated with 5-lipoxygenase and cyclooxygenase and are useful in the treatment of inflammatory disorders.

16 Claims, No Drawings

ACETYLENIC 1,5-DIARYLPYRAZOLES AS ANTIINFLAMMATORY AGENTS

This application claims benefits of provisional application 60,058,295 filed Sep. 9, 1997.

The present invention relates to substituted pyrazole derivatives, methods of their manufacture, intermediates used in their manufacture and pharmaceutical compositions containing them. These compounds inhibit the production of the arachidonic acid products associated with 5-lipoxygenase and cyclooxygenase, namely, 5-HETE, $TXB_2$ and $PgD_2$ respectively.

BACKGROUND OF THE INVENTION

Leukotrienes are a family of endogenous metabolites of arachidonic acid which play an integral role in regulating inflammatory events. Since their discovery in the late seventies, many have worked to determine the biosynthesis of leukotrienes with an eye toward mediating inflammatory responses. Much of this work has focused on the enzymes used in the conversion of arachidonic acid to leukotrienes and prostaglandins, namely 5-lipoxygenase (5-LO) and cyclooxygenase (CO). The present invention relates to substituted pyrazole derivatives, and more particularly, to 1,5-diphenyl-1-propyn-3-ylpyrazoles. These compounds inhibit the production of the arachidonic acid products associated with 5-lipoxygenase and cyclooxygenase, namely, 5-HETE and $PgD_2$ respectively. These compounds inhibit the production of 5-HETE and $PgD_2$ at doses equal to or below other pharmacologically active 5-LO and CO inhibitors. In addition to the aforementioned in vitro screens, particular compounds of the invention inhibit the production of leukotriene $B_4$ ($LTB_4$), a 5-LO product and prostaglandin ($TXB_2$), a CO product in an animal model. Therefore, compounds of the invention are potentially useful in alleviating inflammatory diseases associated with these products such as asthma, arthritis, hypersensitivity, myocardial ischemia, dermatological conditions such as psoriasis and dermatitis, and gastrointestinal inflammatory conditions, such as, inflammatory bowel syndrome in mammals. The compounds may also be employed to treat or suppress the signs or symptoms of adult respiratory distress syndrome. Although some compounds of the invention effectively inhibit on the products of either 5-LO or CO, there are some compounds which inhibit both enzymes. These dual inhibitors are believed to be useful in treating both acute and chronic stages of inflammatory disease states.

Although there are other agents which inhibit 5-LO and CO, due to the therapeutic utility of these compounds, further compounds having this utility are desired.

SUMMARY OF THE INVENTION

The inventions relates to novel compounds of the Formula I

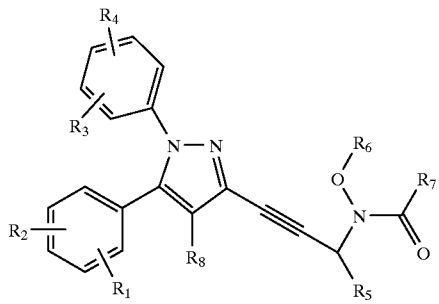

wherein:

$R_1$, $R_2$, $R_3$, and $R_4$ are independently selected from the groups consisting of hydrogen, $C_{1-5}$alkyl, $C_{1-5}$alkoxy, phenyl, halo, hydroxy, $C_{1-5}$alkylsulfonyl, $C_{1-5}$alkylthio, trihalo$C_{1-5}$alkyl, amino, nitro and 2-quinolinylmethoxy;

$R_5$ is hydrogen, $C_{1-5}$alkyl, trihalo$C_{1-5}$alkyl, phenyl, substituted phenyl where the phenyl substitutents are halogen, $C_{1-5}$alkoxy, trihalo$C_{1-5}$alkyl or nitro or $R_5$ is heteroaryl of 5–7 ring members where at least one of the ring members is nitrogen, sulfur or oxygen;

$R_6$ is hydrogen, $C_{1-5}$alkyl, phenyl $C_{1-5}$alkyl, substituted phenyl $C_{1-5}$alkyl where the phenyl substitutents are halogen, $C_{1-5}$alkoxy, trihalo$C_{1-5}$alkyl or nitro, or $R_6$ is $C_{1-5}$alkoxycarbonyl, phenoxycarbonyl, substituted phenoxycarbonyl where the phenyl substitutents are halogen, $C_{1-5}$alkoxy, trihalo$C_{1-5}$alkyl or nitro;

$R_7$ is $C_{1-10}$alkyl, substituted $C_{1-10}$alkyl where the substituents are halogen, trihalo$C_{1-5}$alkyl, $C_{1-5}$alkoxy, carboxy, $C_{1-5}$alkoxycarbonyl, amino, $C_{1-5}$alkylamino, di$C_{1-5}$alkylamino, di$C_{1-5}$alkylamino$C_{1-5}$alkylamino, $C_{1-5}$alkylamino$C_{1-5}$alkylamino or a heterocycle containing 4–8 ring atoms where one more of the ring atoms is nitrogen, oxygen or sulfur, where said heterocycle may be optionally substituted with $C_{1-5}$alkyl; or $R_7$ is phenyl, substituted phenyl (where the phenyl substitutents are one or more of $C_{1-5}$alkyl, halogen, $C_{1-5}$alkoxy, trihalo$C_{1-5}$alkyl or nitro), or $R_7$ is heteroaryl having 5–7 ring atoms where one or more atoms are nitrogen, oxygen or sulfur, fused heteroaryl where one or more 5–7 membered aromatic rings are fused to the heteroaryl, or $R_7$ is $NR_9R_{10}$ where $R_9$ and $R_{10}$ are independently selected from hydrogen and $C_{1-5}$alkyl or $R_9$ and $R_{10}$ may be taken together with the depicted nitrogen to form a heteroaryl ring of 5–7 ring members where one or more of the ring members is nitrogen, sulfur or oxygen where said heteroaryl ring may be optionally substituted with $C_{1-5}$alkyl;

$R_8$ is hydrogen, $C_{1-5}$alkyl, nitro, amino, and halogen;

and pharmaceutically acceptable salts thereof.

An additional formula of the invention is Formula II

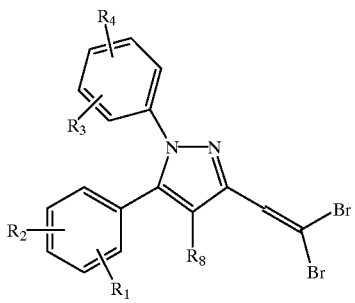

II wherein:

$R_1$, $R_2$, $R_3$, and $R_4$ are independently selected from the groups consisting of hydrogen, $C_{1-5}$alkyl, $C_{1-5}$alkoxy, phenyl, halo, hydroxy, $C_{1-5}$alkylsulfonyl, $C_{1-5}$alkylthio, trihalo$C_{1-5}$alkyl, amino, nitro and 2-quinolinylmethoxy;

$R_8$ is hydrogen, $C_{1-5}$alkyl, nitro, amino, and halogen.

Compounds of Formula II are useful as novel intemediates used in the manufacture of Compounds of Formula I.

Further compounds of the invention are compounds of Formula III

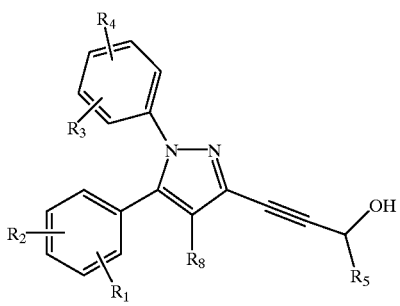

III wherein:

$R_1$, $R_2$, $R_3$, and $R_4$ are independently selected from the groups consisting of hydrogen, $C_{1-5}$alkyl, $C_{1-5}$alkoxy, phenyl, halo, hydroxy, $C_{1-5}$alkylsulfonyl, $C_{1-5}$alkylthio, trihalo$C_{1-5}$alkyl, amino, nitro and 2-quinolinylmethoxy;

$R_5$ is hydrogen, $C_{1-5}$alkyl, trihalo$C_{1-5}$alkyl, phenyl, substituted phenyl where the phenyl substitutents are halogen, $C_{1-5}$alkoxy, trihalo$C_{1-5}$alkyl or nitro or heteroaryl of 5–7 ring members where at least one of the ring members is nitrogen, sulfur or oxygen;

$R_8$ is hydrogen, $C_{1-5}$alkyl, nitro, amino, and halogen.

Said compounds are also novel and useful in the synthesis of compounds of Formula I.

DETAILED DESCRIPTION OF THE INVENTION

The terms used in describing the invention are commonly used and known to those skilled in the art. However, the terms that could have other meanings are defined. "HBSS" refers to Hank's Balanced Salt Solution. "Independently" means that when there are more than one substituent, the substitutents may be different. The term "alkyl" refers to straight, cyclic and branched-chain alkyl groups and "alkoxy" refers to O-alkyl where alkyl is as defined supra. "LDA" refers to lithium diiopropylamide, and "LAH" refers to lithium aluminum hydride. "DMF" refers to N,N-dimethylforamide, "EtOAc" refers to ethyl acetate, "MeOH" refers to methanol, and "THF" refers to tetrahydrofuran. The term "MPLC" refers to medium pressure liquid chromatography.

The symbol "Ph" refers to phenyl, and "aryl" includes mono and fused aromatic rings such as phenyl and naphthyl. The term heterocycle refers to any non-aromatic cyclic compound which contains one or more heteroatom, selected from nitrogen, oxygen or sulfur. Examples of such heterocycles include, but are not limited to piperidine, pyrrolidine, piperazine, morpholine, tetrahydrofuran, and 1,4-dioxane. The term heteroaryl refers to aromatic rings containing one or more heteroatoms. Example of such heteroaryl compounds include abut are not limited to, furan, thiophene, pyridine, pyrazine, imidazole, and azepine. Fused heteroaryls refer to compounds where the heteroaryl is fused to another aromatic ring. Examples of such heteroaryls include but are not limited to indole, benzimidazole, benzothiazole, benzodiazepine, quinoline, and isoquinoline.

The compounds of the invention may be prepared as illustrated by the following schemes. As illustrated by Scheme 1 to prepare a compound where $R_1$ is H, $R_2$ is Cl, $R_3$ is hydrogen, $R_4$ is 2-quinolinylmethoxy $R_5$ is $C_4H_9$ and $R_6$ is hydrogen, and $R_7$ is 1-(4-methylpiperazine), an appropriately substituted acetophenone, 1a is used as a starting material. 4'-Chloroacetophenone is treated with a strong base such as lithium hexamethyldisilazide/THF at about −70 to −20° C. over 30 min in a suitable solvent such as THF under an inert atmosphere such as $N_2$. Once anion formation is complete, this material is treated with ethyl diethoxyacetate at 0° C. to room temperature over several days to give the diketone 1b. This ketone may be treated with an appropriately substituted hydrazine such as 4-methoxyphenylhydrazine and a mild base such as $NaHCO_3$ in a suitable solvent such as MeOH at room temperature to reflux over 24 h to give the pyrazole 1c. Treatment of 1c with a halogen source such as carbon tetrabromide and triphenylphosphine at 0° C. to room temperature over 5 h gives the dibromide 1d. This intermediate may be treated with HBr at room temperature to give the hydroxy derivative 1e. Treatment of this intermediate with a mild base such as $K_2CO_3$ and 2-(chloromethyl)quinoline and an inert solvent such as acetone at reflux over 16 h give the methylquinoline substituted dibromide 1f. Treatment of 1f with tetrabutylammonium fluoride in THF at about room temperature for about 24 h under $N_2$ gives the acetylene 1g. Acetylene 1g may be treated with a strong base such as n-BuLi in a suitable solvent such as THF at about −78° C. over 1 h and subsequently treated with an aldehyde, 1h, at about −78° C. to room temperature over about 5 h to give the hydroxy compound 1i. Treatment of 1i with diethyl azodicarboxylate, N,O-bis(phenoxycarbonyl) hydroxylamine, and tripheynylphosphine in a suitable solvent such as THF gives the Mitsunobu product 1j. Intermediate 1j may subsequently be treated with 4-methylpiperazine in a solvent such as MeOH at room temperature to 50° C. for about 3–48 h to give the desired compound of Formula I where $R_1$ is H, $R_2$ is Cl, $R_3$ is hydrogen, $R_4$ is 2-quinolinylmethoxy, $R_5$ is $C_4H_9$ and $R_6$ is hydrogen, and $R_7$ is 1-(4-methylpiperazine).

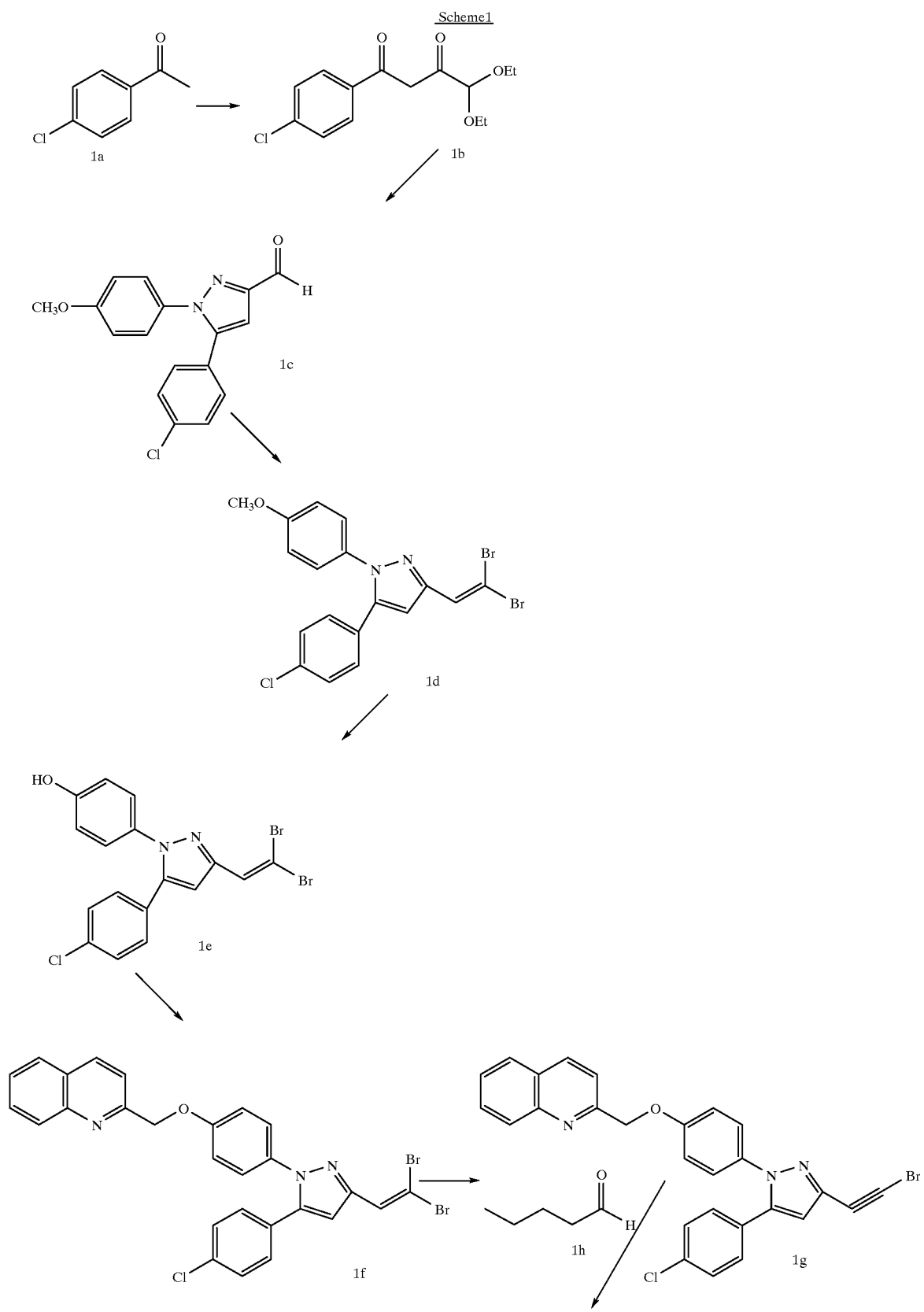

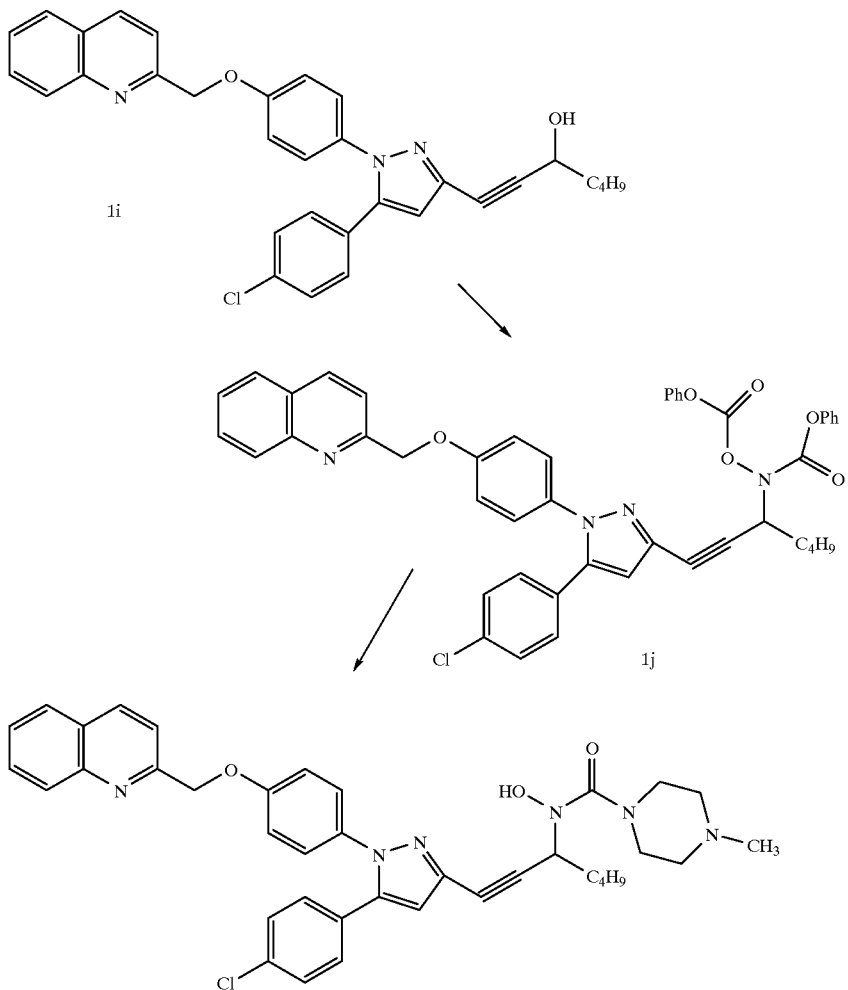

Intermediate 1i may be used as the starting material to prepare a compound of the invention where $R_1$ is H, $R_2$ is Cl, $R_3$ is hydrogen, $R_4$ is 2-quinolinylmethoxy, $R_5$ is $C_4H_9$ and $R_6$ is hydrogen, and $R_7$ is piperidin-1-yl. Treatment of 1i with diethyl azodicarboxylate, N,O-bis(t-butoxycarbonyl) hydroxylamine, and tripheynylphosphine in a suitable solvent such as THF gives the Mitsunobu product 2a. Intermediate 2a may be hydrolyzed with trifluoroacetic acid or HCl to give the hydroxylamine 2b. Treatment of 2b with an appropriately substituted acyl halide, such as chloroacetyl chloride, gives the acylated intermediate 2c. This intermediate may be treated with an amine such as piperidine in a suitable solvent such as DMF at room temperature over 2–24 h to give the desired compound of the invention.

Scheme 2

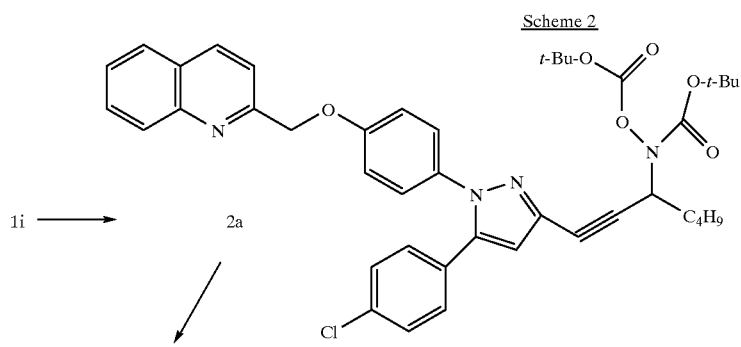

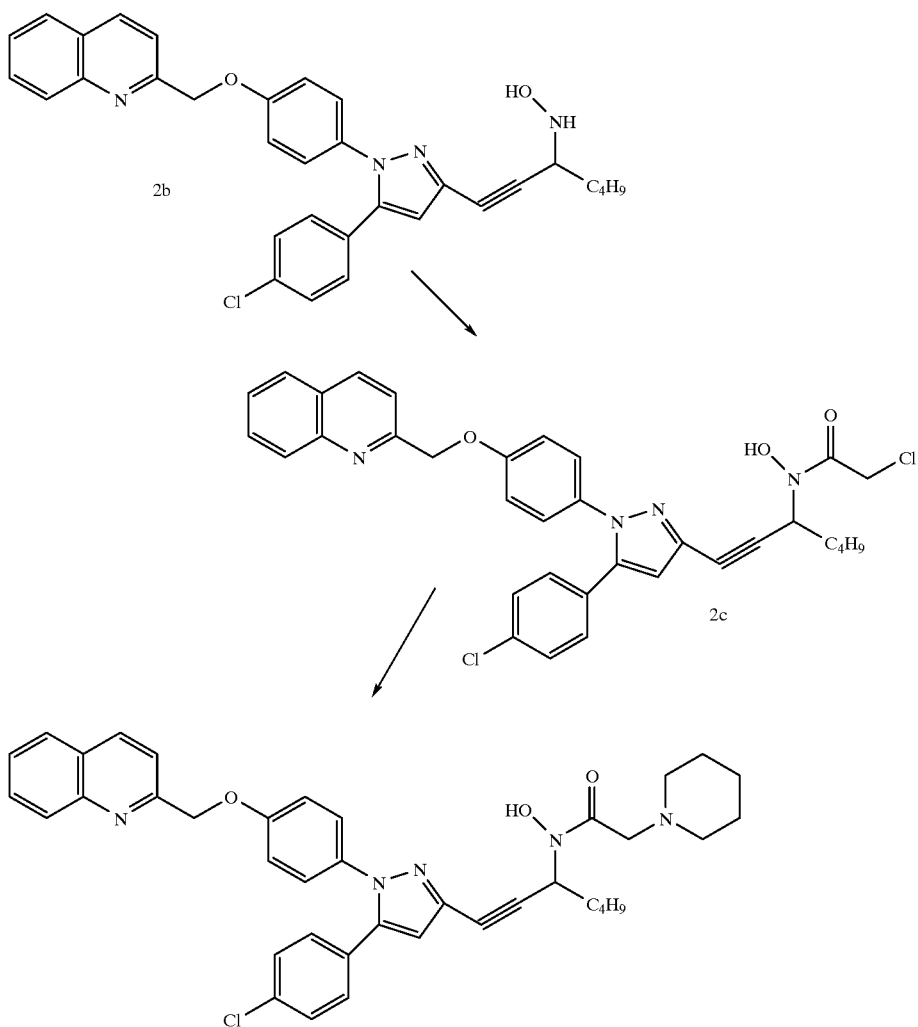

Intermediate 2b may be used to prepare other compounds of the invention as illustrated by Scheme 3. Treatment of the hydroxylamine 2b with an acylating agent, such as thiazol-2-yl chloride, a 3-fold excess of an organic base such as pyridine in a suitable solvent such as $CH_2Cl_2$ gives the bis-acylated intermediate 3a. Hydrolysis of this intermediate with an aqueous base such as NaOH in a suitable solvent such as MeOH gives the illustrated product.

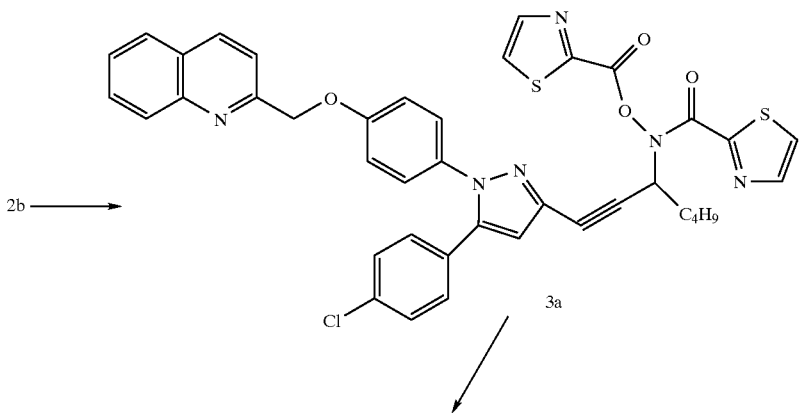

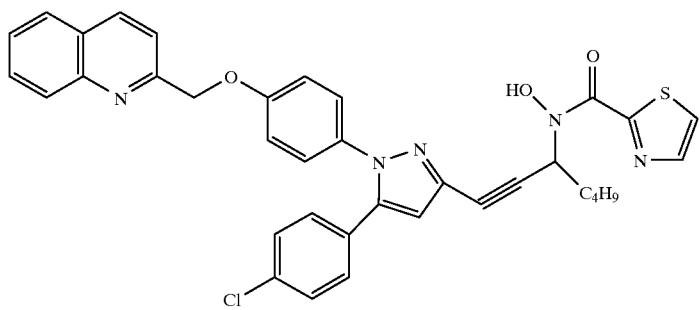

To prepare compounds of the invention where $R_8$ is halogen, Scheme 4 is used. Treatment of intermediate 1f with N-bromosuccinimide in carbon tetrabromide at room temperature over 24 h give the 4-bromo intermediate 4a. Intermediate 4a treated with tetrabutylammonium fluoride in THF at about room temperature for about 24 h under $N_2$ gives the acetylene 4b. Acetylene 4b may be treated with a strong base such as n-BuLi in a suitable solvent such as THF at about −78° C. over 1h and subsequently treated with an aldehyde, 1h, at about −78° C. to room temperature over about 5 h to give the hydroxy compound 4c. Treatment of 1i with diethyl azodicarboxylate, N,O-bis(t-butoxycarbonyl) hydroxylamine, and tripheynylphosphine in a suitable solvent such as THF gives the Mitsunobu product 4d. Intermediate 4d may be hydrolyzed with trifluoroacetic acid or HCl to give the hydroxylamine 4e. Treatment of 4e with an appropriately substituted acyl halide, such as methyl chloroformate gives the bisacylated product 4f. Hydrolysis of this intermediate with an aqueous base such as NaOH in a suitable solvent such as MeOH gives the illustrated product.

Scheme 4

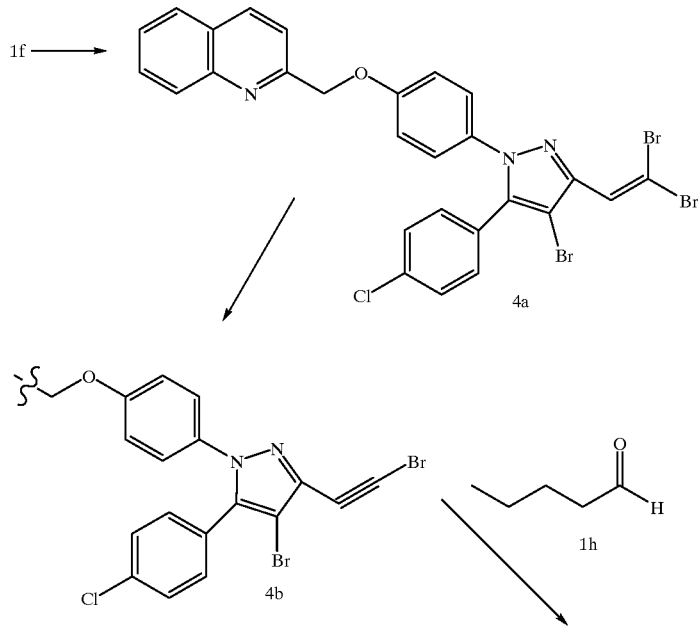

-continued

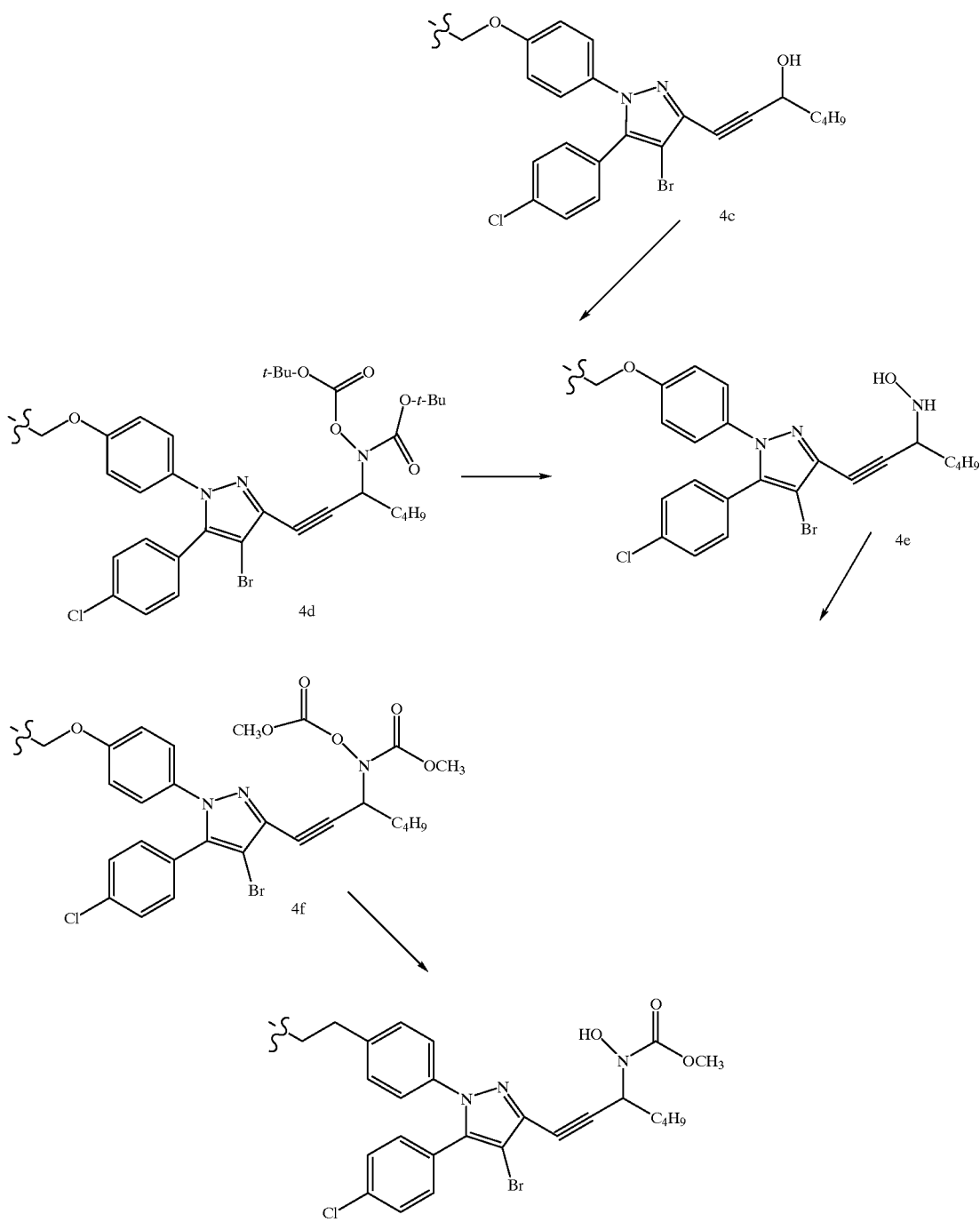

The compounds of the invention were evaluated for their ability to inhibit the production of the arachidonic acid by-products in broken and whole cell models.

Procedure I was used to determine the ability of the compounds to inhibit cyclooxygenase. Sheep seminal vesicle (SSV) cyclooxygenase (95% pure, prostaglandin endoperoxide synthase, EC 1.14.99.1 specific activity 24 units/mg protein) obtained as a lyophilized powder from Biomol (Plymouth Meeting, PA) was reconstituted at a concentration of 59 mg/mL in Hanks' Balanced Salt Solution (HBSS). The enzyme was divided into 200 μL aliquots, snap frozen with liquid $N_2$, and stored at −70° C. until immediately prior to use. Measurements of CO activity were carried out in polypropylene tubes containing 495 μL of HBSS to which was added 5 μL of inhibitor or dimethylsulfoxide (DMSO; vehicle control) and 6 μL of SSV CO solution. The tubes were mixed on a vortex shaker, preincubated for 5 min at 37° C. prior to the initiation of the reaction. The reaction was started by the addition of [$^{14}$C]-arachidonic acid (1-$^{14}$C-AA, Amersham, Arlington Heights, Ill.) in 10 μL of methanol. Tubes were again vortexed and incubated in a water bath for 20 minutes after which the tubes were removed and the reaction stopped by acidification with the addition of 1 mL 2M formic acid. Lipophilic products were extracted with 3 mL chloroform and concentrated to dryness under $N_2$. Each pellet was reconstituted with 40 μL of chloroform and spotted on a Whatman Silicon thin-layer chromatography plate and developed in a chromatography tank containing A-9 solvent (11:5:2:1 V:V:V:V, ethyl acetate:trimethyl-pentane:acetic acid:double distilled-$H_2O$). Radioactive cyclooxygenase products (prostaglandin $D_2$, prostaglandin $E_2$, etc.) were measured using a Bioscan System 200 Imaging Scanner. Inhibition of enzyme activity was calculated by comparing the areas under the curve produced in the presence or absence of test compound.

Procedure II was used to assess LO and CO activity. Rat basophilic leukemia cells (RBL-1; $5 \times 10^7$ viable cells/mL) were disrupted by homogenization on ice (four 20 sec bursts) with a Brinkman polytron. Complete cell breakage was verified microscopically. The homogenate was then centrifuged at 9,220×g for 48 minutes at 4° C. The pellet was discarded and the supernatant was saved as the source of enzymes. The supernatant was pre-incubated for five minutes at 37° C. in the presence of 2 mM of $CaCl_2$ and compound or vehicle (1% DMSO). The conversion of AA into products by CO and LO was initiated by adding 10 μL (50 μCi) of 1-$^{14}$C-AA to each tube and incubated at 37° C. for 20 minutes. The reaction was stopped by adjusting the pH of each sample to 3 to 3.5 with 2M formic acid. Samples were extracted with three volumes of chloroform to isolate the products of 5-LO formed during the reaction. Fractions were dried under nitrogen, then resuspended in 40 μL of chloroform and spotted onto silica gel HL plates. The plates were developed in A-9 solvent. The dried plates were analyzed using a Bioscan Imaging TLC scanner to determine the percentage of radiolabelled AA converted to 5-HETE (LO product) in each sample. The percentage of inhibition was calculated by:

[1-(5-HETE test)]/5-HETE control×100=% inhibition

The $IC_{50}$ was determined using a curve fit in Cricket Graph (Computer Associated), which provided the equation of the regressed line used in the calculation.

In Procedure III, the ability to inhibit 5-LO and CO in intact RBL-1 cells was also evaluated. RBL-1 cells were maintained in culture in minimal essential medium (Bio*Whittaker, Walkersville, Md.), containing 12.5% fetal calf serum, 10 mg/mL streptomycin, 10 I.U./mL penicillin G, 50 mg/mL gentamycin and 2 mM L-glutamine (Bio*Whittaker, Walkersville, Md.). Cells were collected by centrifugation, washed once in HBSS, and resuspended at a concentration of $1 \times 10^5$ cells/mL. Cells were incubated in the presence of vehicle or drug then centrifuged at 800×g for 10 minutes at 4° C. The supernatant was removed by aspiration and the cells were resuspended in 0.5 mL of HBSS. The reaction was started by the addition of 20 μg/mL of calcium ionophore A 23187 (mixed calcium and magnesium salts, Calbiochem, La Jolla Calif.) and allowed to proceed for 15 minutes, then stopped by plunging the tubes into a slush ice bath. The conversion of AA to 5-LO products was initiated by the addition of 10 μL (50 μCi) of 1-$^{14}$C-AA. Products were isolated by acidification and extraction, followed by thin layer chromatography analysis as described above. Radioactive areas corresponding to authentic 5-LO (5-HETE) and CO ($PgD_2$) products were quantitated by the Bioscan 2000 Imaging System and the $IC_{50}$ was calculated as above.

Tables I–IV list the experimental results of procedures I–III for select compounds of the invention. Either $IC_{50}$s (□M) or the % inhibition @ 10 □M are listed.

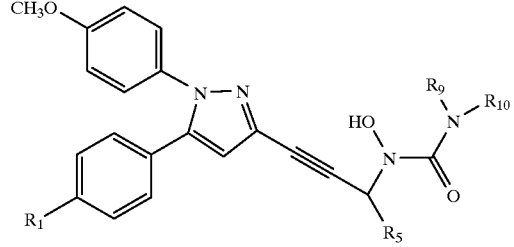

TABLE I

| Cpd | $R_1$ | $R_5$ | $R_9$ | $R_{10}$ | Proc. I | Proc. II CO | Proc. II 5-LO | Proc. III CO | Proc. III 5-LO |
|---|---|---|---|---|---|---|---|---|---|
| 1 | Me | H | H | H | 1.02 | 0.31 | 0.07 | 12.1 | 4.7 |
| 2 | Me | Me | H | H | (10%) | 9.4 | 0.37 | 1.4 | 7.7 |
| 3 | Me | Et | H | H | (22%) | 15.9 | 0.07 | 2.1 | 21.3 |
| 4 | Me | i-Pr | H | H | (29%) | 4.6 | 0.24 | 1.2 | 8.4 |
| 5 | Cl | H | H | H | (9%) | (0%) | 0.08 | | 0.9 |
| 6 | Cl | Me | H | H | 32 | (0%) | 0.01 | 6.2 | 3.5 |
| 7 | Cl | Me | H | Me | (5%) | (0%) | (79%) | | |
| 8 | Cl | Me | H | n-Pr | (14%) | (32%) | (82%) | | 2.8 |
| 9 | Cl | Me | $(CH_2)_5$ | | (44%) | (82%) | (76%) | 0.69 | 8 |
| 10 | Cl | Me | $(CH_2)_2O(CH_2)_2$ | | (14%) | (58%) | (81%) | 1.6 | 12 |
| 11 | Cl | Et | H | H | (0%) | (30%) | (91%) | 70.4 | 2.17 |
| 12 | Cl | i-Pr | H | H | (38%) | (0%) | (90%) | 14.5 | 3.9 |

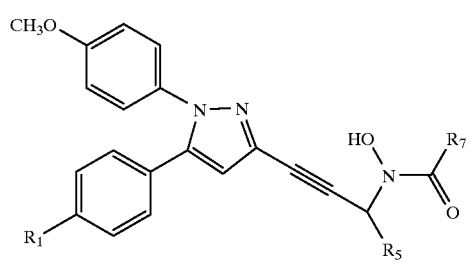

TABLE II

| Cpd | $R_1$ | $R_5$ | $R_7$ | Proc. I | Proc. II CO | Proc. II 5-LO | Proc. III CO | Proc. III 5-LO |
|---|---|---|---|---|---|---|---|---|
| 13 | Me | H | Me | (74%) | (100%) | (100%) | 0.03 | 7.2 |
| 14 | Me | H | Et | (79%) | (100%) | (100%) | 0.06 | 3 |
| 15 | Me | H | Ph | (52%) | (83%) | (100%) | 0.93 | 8 |
| 16 | Me | H | 4-pyridyl | (17%) | (66%) | (89%) | 5.5 | 26.6 |
| 17 | Me | H | OMe | (74%) | (100%) | (100%) | 0.28 | 8.8 |
| 18 | Me | Me | Me | 0.31 | 0.01 | 0.08 | 0.11 | 13.1 |
| 19 | Me | Me | Et | (76%) | (67%) | (93%) | | |
| 20 | Me | Me | i-Pr | 0.39 | 0.04 | 0.1 | 0.09 | 5.6 |
| 21 | Me | Me | $CH_2Cl$ | 1.2 | (100%) | (100%) | 0.36 | 23.6 |
| 22 | Me | Me | $CH_2CH_2CO_2Et$ | 2.93 | (100%) | (97%) | 10 | 10.1 |
| 23 | Me | Me | $CF_3$ | 0.42 | 0.05 | 1.66 | 0.19 | 23.5 |
| 24 | Me | Me | $CO_2Et$ | (66%) | (50%) | (71%) | 3.4 | 8.5 |
| 25 | Me | Me | 2-furyl | 1.3 | (61%) | (70%) | 2.9 | 2.9 |
| 26 | Me | Me | 3-pyridyl | 6 | (54%) | (88%) | 11.5 | 25.4 |
| 27 | Me | Me | Ome | 0.53 | 0.14 | 0.28 | 0.49 | 7.1 |
| 28 | Me | Et | Me | 0.43 | 0.01 | 0.07 | 0.22 | 10.7 |

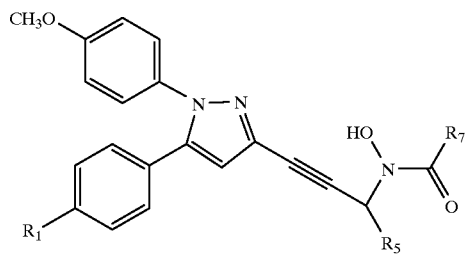

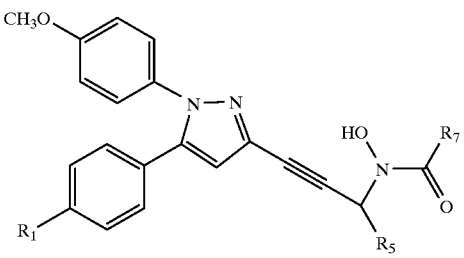

TABLE III

| Cpd | $R_1$ | $R_5$ | $R_7$ | Proc. I | Proc. II CO | Proc. II 5-LO | Proc. III CO | Proc. III 5-LO |
|---|---|---|---|---|---|---|---|---|
| 29 | Et | Me | Me | 2.51 | 0.06 | 0.27 | 0.34 | 11.9 |
| 30 | Et | Me | i-Pr | 0.59 | (73%) | (93%) | 0.18 | 13.1 |
| 31 | Et | Me | $CH_2Cl$ | 6.1 | (86%) | (100%) | 1.7 | 36.8 |
| 32 | Et | Me | $CH_2CH_2CO_2Et$ | (3%) | (52%) | (97%) | 14 | 5.1 |
| 33 | Et | Me | $CH_2CH_2CO_2H$ | (0%) | (0%) | (37%) | | |
| 34 | Et | Me | OMe | (21%) | (72%) | (78%) | 0.75 | 57.4 |
| 35 | Cl | Me | Me | 2.54 | 0.03 | 0.11 | 0.16 | 8.1 |
| 36 | Cl | Me | Et | | (100%) | (100%) | | |
| 37 | Cl | Me | i-Pr | | (80%) | (100%) | | |
| 38 | Cl | Me | $n-C_7H_{15}$ | (31%) | (21%) | (100%) | | |
| 39 | Cl | Me | $CH_2CH_2CO_2H$ | (0%) | (0%) | (74%) | | |
| 40 | Cl | Me | Ph | (5%) | 14.9 | 0.92 | 5.5 | 1.8 |
| 41 | Cl | Me | Ome | 1.62 | (84%) | (77%) | 0.29 | 8.7 |

TABLE IV

| Cpd | $R_1$ | $R_5$ | $R_7$ | Proc. I | Proc. II CO | Proc. II 5-LO | Proc. III CO | Proc. III 5-LO |
|---|---|---|---|---|---|---|---|---|
| 42 | Me | Me | $CH_2NH(CH_2)_3NMe_2$ | (0%) | (14%) | (29%) | | |
| 43 | Me | Me | $CH_2$imidazol-1-yl | 10 | (13%) | (67%) | 3.6 | 38.7 |
| 44 | Et | Me | $CH_2$morpholin-4-yl | (0%) | (0%) | (93%) | | |
| 45 | Et | Me | $CH_2$-4-methyl-piperazin-1-yl | (0%) | (11%) | (25%) | | |

The activity of select compounds is demonstrated by Procedure IV, an ex vivo eicosanoid synthesis assay using dogs. Adult beagle or mongrel dogs (10–15 kg) of either sex were fasted overnight prior to the initiation of each experiment. The forelimb was clipped and swabbed with an alcohol prep (70% isopropanol). Blood was drawn by venipuncture into syringes containing lithium heparin (Starstead, Newton, N.C.) immediately prior to administration of compound or vehicle and then at various intervals following dosing. The test compound was administered orally as a suspension in 0.5% methocel. At various times after dosing, blood samples were drawn and placed on an electric rocker platform to assure complete and continuous mixing. White blood cell (wbc) counts were performed using a Sysmex hematology analyzer. This was done in an effort to normalize the number of leukocytes to be stimulated with calcium ionophore. A 1.0 mL aliquot of whole blood was challenged with 50 μL of a $2.6 \times 10^{-5}$M solution of calcium ionophore A23187 (Calbiochem, La Jolla, Calif.) prepared in DMSO and diluted in in HBSS. After a 15 minute incubation at 37° C., the reaction was stopped by placing the samples in an ice bath (4° C.) for 5 minutes and then centrifuging at 11,000×g for 5 minutes to separate the plasma fraction from blood cells. The plasma fraction was removed, diluted in an appropriate buffer, and analyzed for the presence of $LTB_4$ and $TxB_2$ by standard RIA techniques. The data is listed in Table V and notes compound, the number of experiments, the time blood was drawn, the dose, and the % inhibition of CO and 5-LO as calculated by standard techniques.

TABLE V

| Cpd | number of experiments | % inh CO 5-LO | | mg/kg | h |
|---|---|---|---|---|---|
| 1 | 3 | 86 | 56 | 5 | 1 |
| 1 | 3 | 82 | 53 | 5 | 2 |
| 1 | 3 | 76 | 32 | 5 | 4 |
| 1 | 3 | 46 | 15 | 5 | 8 |
| 1 | 3 | 11 | 10 | 5 | 24 |
| 35 | 2 | 92 | 34 | 5 | 2 |
| 35 | 2 | 75 | 20 | 5 | 4 |
| 35 | 2 | 81 | 26 | 5 | 6 |
| 35 | 2 | 62 | 31 | 5 | 8 |
| 35 | 2 | 68 | 12 | 5 | 24 |

As indicated by the biological activity, the compounds of Formula I may be used in pharmaceutical compositions to treat patients (humans and other primates) with disorders related to inflammation. The preferred route is oral administration, however compounds may be administered by intravenous infusion. Oral doses range from about 1–25 mg/kg daily. Infusion doses can range from about 0.01–1 mg/kg/min of inhibitor, admixed with a pharmaceutical carrier over a period ranging from several minutes to several days.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

Although compounds of the invention are useful as anti-inflammatory agents some compounds are more active than others and are either preferred or particularly preferred.

The preferred compounds of Formula I include the compounds:

N-hydroxy-N-(1-(1-(4-methoxyphenyl)-5-(4-methylphenyl)pyrazol-3-yl)-1-butyn-3-yl)urea.

N-hydroxy-N-(1-(5-(4-chlorophenyl)-1-(4-methoxyphenyl)pyrazol-3-yl)-1-propyn-3-yl)urea.

N-acetyl-N-(1-(1-(4-methoxyphenyl)-5-(4-methylphenyl)pyrazol-3-yl)-1-propyn-3-yl)hydroxylamine.

N-methoxycarbonyl-N-(1-(1-(4-methoxyphenyl)-5-(4-methylphenyl)pyrazol-3-yl)-1-propyn-3-yl)hydroxylamine.

N-isobutyryl-N-(1-(1-(4-methoxyphenyl) -5(4-methylphenyl)pyrazol-3-yl)-1-butyn-3-yl)hydroxylamine.

N-trifluoroacetyl-N-(1-(1-(4-methoxyphenyl)-5-(4-methylphenyl)pyrazol-3-yl)-1-butyn-3-yl)hydroxylamine.

N-(furan-2-carbonyl)-N-(1-(1-(4-methoxyphenyl)-5-(4-methylphenyl)pyrazol-3-yl)-1-butyn-3-yl)hydroxylamine.

N-acetyl-N-(1-(1-(4-methoxyphenyl)-5-(4-methylphenyl)pyrazol-3-yl)-1-pentyn-3-yl)hydroxylamine.

N-acetyl-N-(1-(5-(4-ethylphenyl)-1-(4-methoxyphenyl)pyrazol-3-yl)-1-butyn-3-yl)hydroxylamine.

N-isobutyryl-N-(1-(5-(4-ethylphenyl)-1-(4-methoxyphenyl)pyrazol-3-yl)-1-butyn-3-yl)hydroxylamine.

N-acetyl-N-(1-(5-(4-chlorophenyl)-1-(4-methoxyphenyl)pyrazol-3-yl)-1-butyn-3-yl)hydroxylamine.

N-methoxycarbony-N-(1-(5-(4-chlorophenyl)-1-(4-methoxyphenyl)pyrazol-3-yl)-1-butyn-3-yl)hydroxylamine.

N-(imidazol-1-yl)acetyl-N-(1-(1-(4-methoxyphenyl)-5-(4-methylphenyl)pyrazol-3-yl)-1-butyn-3-yl)hydroxylamine.

The particularly preferred compositions of Formula I include compounds where:

$R_1$ is $C_{1-5}$alkyl or chlorine;

$R_2$ and $R_3$ are hydrogen;

$R_4$ is $C_{1-5}$alkoxy;

$R_5$ is hydrogen or $C_{1-5}$balkyl;

$R_6$ is hydrogen;

$R_7$ is piperidin-1-yl, amino, $C_{1-5}$alkyl, or $C_{1-5}$alkoxy; and $R_8$ is hydrogen.

In order to illustrate the invention the following examples are included. These examples do not limit the invention. They are meant only to suggest a method of practicing the invention. Those skilled in the art may find other methods of practicing the invention, which are obvious to them. However those methods are deemed to be within the scope of this invention.

EXAMPLES

Unless otherwise noted, materials used in the examples were obtained from commercial suppliers and were used without further purification. Melting points were determined on a Thomas Hoover apparatus and are uncorrected. Proton nuclear magnetic resonance (1H NMR) spectra were measured in the indicated solvent with tetramethylsilane (TMS) as the internal standard using Bruker AC-300 (300 MHz) and General Electric QE-300 (300 MHz) spectrometers. NMR chemical shifts are expressed in parts per million (ppm) downfield from internal TMS using the d scale. $^1$H NMR data are tabulated in order: multiplicity, (s, singlet; d, doublet; t, triplet; q, quartet; m, multiplet), number of protons, coupling constant in Hertz). Infrared (IR) spectra were determined on a Nicolet 5DXB FT-IR spectrophotometer. Chemical ionization (DCI) and fast atom bombardment (FAB) mass spectra (MS) were determined on Finnegan MAT 8230 and Fisons Trio 1000 spectrometers. Elemental analyses were performed by Quantitative Technologies, Inc. (QTI), PO Box 470, Salem Industrial Park, Bldg #5, Whitehouse, N.J. 08888-0470. Analytical thin layer chromatography (TLC) was done with Merck Silica Gel 60 $F_{254}$ plates (250 micron). Medium pressure liquid chromatography (MPLC) was done with Merck Silica Gel 60 (230–400 mesh).

Example 1

1-(4'-Methylphenyl)-4,4-diethoxybutan-1,3-dione (Cpd. 46). A 1.0M solution of lithium hexamethyldisilazide in THF (310 mmol, 310 mL) was diluted with 20 mL of THF and cooled to −70° C. (internal temperature) with an acetone/dry ice bath under $N_2$. A solution of 4'-methylacetophenone (150 mmol, 20.1 g, 20 mL) in 50 mL of tetrahydrofuran (THF) was added dropwise over a 15 min period, keeping the internal temperature below −60° C. After 1 h, the cooling bath was removed and the temperature was allowed to rise to −25° C. The reaction flask was immersed in an ice/acetone bath and a solution of ethyl diethoxyacetate (160 mmol, 28 g, 28.6 mL) in 20 mL of THF was added dropwise; during the addition, the internal temperature was kept below 0° C. The brown-red solution was stirred for 24 h and was re-cooled to 0° C. Aqueous HCl (3N, 618 mmol, 206 mL) was added carefully (temperature kept below 20° C.) to bring the pH to 3–4. The layers were separated and the aqueous layer was extracted with 200 mL of ether. The combined organic layers were washed twice with brine, dried over $Na_2SO_4$, and concentrated to give 40.3 g (100%) Cpd. 46 as an orange oil; $^1$H NMR (CDCl$_3$, 300 MHz) 1.30 (t, 6H, J=7), 2.42 (s, 3H), 3.5–3.8 (complex, 4H), 4.90 (s, 1H), 6.58 (s, 1H), 7.28 (d, 2H, J=8), 7.74 (d, 2H, J=8), 15.8 (broad s, 1H).

Example 2

General procedure for the preparation of substituted 4,4-diethoxy-1-phenylbutan-1,3-diones. A 1.0M solution of lithium hexamethyldisilazide in THF (105 mmol) was diluted with 10–20 mL of THF and cooled to −70° C. (measured internally) under $N_2$ in an acetone/dry ice bath. A solution of the appropriately substituted acetophenone (50 mmol) in 10–20 mL of ether or THF was added dropwise, keeping the internal temperature below −60° C. After 15–60 min, the cooling bath was removed and the internal temperature was allowed to rise to −20° C. The reaction flask was immersed in an ice/acetone bath and a solution of ethyl diethoxyacetate (55 mmol) in 10 mL of THF was added dropwise; during the addition, the internal temperature was kept below 0° C. When the addition was complete, the reaction mixture was allowed to warm to room temperature stir for 1–3 days. The mixture was cooled in an ice bath and 3N or 6N aqueous HCl (210 mmol) was added carefully to bring the pH to 2–4, keeping the internal temperature below 20° C. The layers were separated and the aqueous layer was extracted with 100–200 mL of ether. The combined organic layers were washed with brine, dried over $Na_2SO_4$, and concentrated to give the desired 4,4-diethoxy-1-phenylbutan-1,3-dione, which was usually used without purification. Some of the diones prepared by this method are listed in Table A

TABLE A

| Cpd | $R_1$ | characterization |
|---|---|---|
| 46 | Me | $^1$H NMR |
| 47 | Et | $^1$H NMR |
| 48 | Cl | $^1$H NMR |

Example 3

1-(4-Methoxyphenyl)-5-(4-methylphenyl)pyrazole-3-carboxaldehyde (Cpd 49)

A suspension of 4-methoxyphenylhydrazine (150 mmol, 26.2 g) and NaHCO$_3$ (180 mMol, 15.1 g) was stirred in 150 mL of MeOH for 1 h. A solution of Cpd. 46 (~150 mmol, 40.3 g) in 150 mL of MeOH was added and the mixture was stirred for 18 h. The mixture was refluxed for 2 h, then was cooled and concentrated using a rotary evaporator to remove MeOH and ethanol. The residue was dissolved in 200 mL of THF and 100 mL of 1N aqueous HCl and refluxed for 1 h. The cooled mixture was diluted with 500 mL of ether and washed with water, saturated aqueous NaHCO$_3$, and brine. After drying over $Na_2SO_4$, the organic solution was concentrated to give 44.3 g of a brown semi-solid which was crystallized from ether/hexanes to give 31.4 g (72%) Cpd. 49; $^1$H NMR (CDCl$_3$, 300 MHz) 2.36 (s, 3H), 3.84 (s, 3H), 6.89, (d, 2H, J=8), 6.97 (s, 1H), 7.12 (s, 4H), 7.25 (d, 2H, J=8), 10.5 (s, 1H). MPLC of the mother liquor using a gradient ranging from 10% to 35% EtOAc/hexanes as eluent provided an additional 6.98 g (16%) of Cpd. 49.

Example 4

General procedure for the preparation of substituted pyrazole-3-carboxaldehydes. A suspension of the appropriately substituted phenyhydrazine hydrochloride (100 mmol) and solid $NaHCO_3$ (120 mmol) was stirred under $N_2$ in 100 mol of methanol. After 1–4 h, a solution of the appropriately substituted 4,4-diethoxy-1-phenylbutan-1,3-dione (100 mmol) in 100 mL of MeOH was added and the mixture was stirred for 2–24 h at room temperature, then was refluxed for 2–4 h. The solvent was removed using a rotary evaporator and the residue was dissolved in a mixture of 50 mL of 1N aqueous HCl and 50–150 mL of THF. The acidic two-phase mixture was refluxed for 1–4 h and, after cooling to room temperature, was partitioned between 200 mL of ether and 200 mL of water. The organic layer was washed with saturated aqueous $NaHCO_3$ and brine, dried over $Na_2SO_4$, and concentrated to give a brown solid which was purified by recrystallization or MPLC to give the desired pyrazole-3-carboxaldehyde. The physical data of some of the aldehydes is listed in Table B

TABLE B

| Cpd | $R_1$ | MS, [M + H]+ |
|---|---|---|
| 49 | Me | 293 |
| 50 | Et | 307 |
| 51 | Cl | 313 |

Example 5

1,1-Dibromo-2-(1-(4-methoxyphenyl)-5-(4-methylphenyl)pyrazol-3-yl)ethylene (Cpd. 52). Carbon tetrabromide (54.6 mmol, 18.1 g) was added in four portions over a 20 min period to a stirring solution of triphenylphosphine (109 mmol, 28.7 g) in 130 mL of $CH_2Cl_2$ under $N_2$. The orange suspension was stirred for 30 min and was cooled in an ice bath. A solution of Cpd. 49 (27.3 mmol, 7.98 g) in 50 mL of $CH_2Cl_2$ was added dropwise and the mixture was stirred for 30 min. The ice bath was removed and the mixture was stirred for 60 min more, then was poured into 950 mL of hexanes with rapid stirring. The resulting slurry was stirred for 20 min and was filtered. The solids were washed thoroughly with hexanes and the combined filtrates were concentrated to give 21.1 g of yellow foam. The foam was dissolved in a minimum amount of $CH_2Cl_2$ (~40 mL) and was stirred rapidly while 300 mL of hexanes was added. The resulting precipitate was filtered and washed thoroughly with hexanes, and the filtrates were combined and concentrated to give 13.9 g of orange oil. The crude product was purified by MPLC using a solvent gradient ranging from 30% $CH_2Cl_2$/hexanes to 100% $CH_2Cl_2$ to give 10.7 g (88%) Cpd. 52 as a yellow oil. The oil was crystallized from methyl t-butyl ether/hexanes to give 7.41 g of Cpd. 52 as a white solid, m.p. 110–111° C.; $^1$H NMR ($CDCl_3$, 300 MHz) 2.34 (s, 3H), 3.81 (s, 3H), 6.85 (d, 2H, J=9), 7.11 (s, 4H), 7.12 (s, 1H), 7.20 (d, 2H, J=9), 7.64 (s, 1H); IR (KBr) 1518, 1245, 845, 791 $cm^{-1}$; MS (DCI) m/z 448 (base), 369. Anal. Calcd for $C_{19}H_{16}Br_2N_2O$: C, 50.92; H, 3.6; N, 6.25. Found: C, 50.84; H, 3.45; N 6.22. The mother liquor was concentrated to give an additional 3.2 g of Cpd 52.

Example 6

General procedure for the preparation of substituted 1,1-dibromo-2-(pyrazol-3-yl)ethylenes. Carbon tetrabromide (20 mmol) was added in four portions over a 20 min period to a stirring solution of triphenylphosphine (40 mmol) in 40 mL of $CH_2Cl_2$ under $N_2$. The orange suspension was stirred for 30 min and was cooled in an ice bath. A solution of the appropriately substituted pyrazole-3-carboxaldehydes (10 mmol) in 10 mL of $CH_2Cl_2$ was added dropwise and the mixture was stirred for 30 min. The ice bath was removed and the mixture was stirred for 60 min more, then was poured into 400 mL of hexanes with rapid stirring. The resulting slurry was stirred for 20 min and was filtered. The solids were washed thoroughly with hexanes and the combined filtrates were concentrated to give 21.1 g of yellow foam. The foam was dissolved in a minimum amount of $CH_2Cl_2$ and was stirred rapidly while 100–200 mL of hexanes was added. The resulting precipitate was filtered and washed thoroughly with hexanes. The filtrates were combined and concentrated to give crude product which was purified by MPLC to provide the desired 1,1-dibromo-2-(pyrazol-3-yl)ethylene. Table C contains some of the analytical data for bromides which were prepared by this method.

TABLE C

| Cpd | $R_1$ | mp, ° C. | MS, [M + H]+ |
|---|---|---|---|
| 52 | Me | 110–111 | 448 |
| 53 | Et | foam | 462 |
| 54 | Cl | 117.5–118.5 | 468 |

Example 7

1-Bromo-2-[1-(4-methoxyphenyl)-5-(4-methylphenyl) pyrazol-3-yl]acetylene (Cpd 55). A solution of Cpd. 52 (15.8 mmol, 7.10 g) in 20 mL of THF was combined with 55.4 mL (55.4 mmol) of a 1M solution of tetra-n-butylammonium fluoride in THF and stirred under $N_2$ at room temperature for 24 h. Water (50 mL) was added and the mixture was extracted with ether. The ether solution was washed with saturated aqueous $NaHCO_3$ and brine, dried over $Na_2SO_4$, and concentrated to give 6.5 g of amber oil. The crude product was purified by MPLC using a solvent gradient ranging from 5% to 15% EtOAc/hexanes; one fraction yielded 1.24 g (21%) of Cpd. 55 as a white solid, m.p. 120–122° C.; $^1$H NMR (CDCl$_3$, 300 MHz) 2.34 (s, 3H), 3.81 (s, 3H), 6.56 (s, 1H), 6.84 (d, 2H, J=9), 7.09 (m, 4H), 7.20 (d, 2H, J=9); IR (KBr) 1516, 1252, 843, 801 cm$^{-1}$; MS (DCI) m/z 367 (base), 289. Anal. Calcd for C$_{19}$H$_{15}$BrN$_2$O: C, 62.14; H, 4.12; N, 7.63. Found: C, 62.44; H, 4.00; N, 7.55. The remaining pure fractions gave an additional 4.36 g (75%) of Cpd. 55.

Example 8

General procedure for the preparation of substituted 1-bromo-2-(pyrazol-3-yl)acetylenes. A solution of the appropriately substituted 1,1-dibromo-2-(pyrazol-3-yl) ethylene (10 mmol) in 15 mL of THF was combined with 35 mmol of a 1M solution of tetra-n-butylammonium fluoride in THF and stirred under N$_2$ at room temperature for 24 h. Water (40–50 mL) was added and the mixture was extracted with ether. The ether solution was washed with saturated aqueous NaHCO$_3$ and brine, dried over Na$_2$SO$_4$, and concentrated to a crude product which was purified by MPLC to give the desired 1-bromo-2-(pyrazol-3-yl)acetylene.

TABLE D

| Cpd | R$_1$ | mp, ° C. | MS, [M + H]+ |
|---|---|---|---|
| 55 | Me | 120–122 | 367 |
| 56 | Et | foam | 381 |
| 57 | Cl | 107–190 | 387 |

Example 9

1-[1-(4-Methoxyphenyl)-5-(4-methylphenyl)pyrazol-3-yl]-1-propyn-3-ol (Cpd. 58). A 1.3M solution of s-butyllithium in cyclohexane (4.43 mmol, 3.41 mL) was added dropwise under N$_2$ to a solution of Cpd. 55 (4.14 mmol, 1.54 g) in 8 mL of THF at −78° C. The pale orange solution was stirred for 45 min and solid paraformaldehyde (8.28 mmol, 0.249 g) was added in one portion under a stream of N$_2$. The solution was allowed to warm slowly to room temperature stir for 3 h. Saturated aqueous NH$_4$Cl (30 mL) was added and the mixture was extracted with ether. The organic layer was washed with brine, dried over Na$_2$SO$_4$, and concentrated to give 1.47 g of yellow foam. The foam was crystallized from 5 mL of ether to give 0.73 g (55%) of Cpd. 58 as an off-white powder. An analytical sample was prepared by recrystallization from hot EtOAc to afford 0.342 g of Cpd. 58 as an off-white solid, m.p. 150–151° C.; $^1$H NMR (CDCl$_3$, 300 MHz) ) 1.93 (t, 1H, J=6.2), 2.34 (s, 3H), 3.81 (s, 3H), 4.51 (d, 2H, J=6.2), 6.56 (s, 1H), 6.84 (d, 2H, J=9), 7.09 (m, 4H), 7.20 (d, 2H, J=9); IR (KBr) 3270 (broad), 1515, 1250, 1032 cm$^{-1}$; MS (DCI) m/z 319 (base), 301. Anal. Calcd for C$_{20}$H$_{18}$N$_2$O$_2$.0.25 H$_2$O: C, 74.40; H, 5.78; N, 8.68. Found: C, 74.26; H, 5.58; N, 8.70.

Example 10

General procedure for the preparation of substituted 1-(pyrazol-3-yl)-1-propyn-3-ols. A solution of s-butyllithium in cyclohexane (11 mmol) or n-butyllithium in hexanes (11 mmol) was added dropwise under N$_2$ to a solution of the appropriately substituted 1-bromo-2-(pyrazol-3-yl)acetylene (10 mmol) in 20 mL of THF or ether at −78° C. The resulting solution was stirred at −78° C. for 45–90 min and the paraformaldehyde or the appropriate aldehyde (20–40mmol) was added neat under an atmosphere of N$_2$. The solution was allowed to warm slowly to room temperature stir for 2–24 h. Saturated aqueous NH$_4$Cl was added and the mixture was extracted with ether, EtOAc, or CH$_2$Cl$_2$. The organic layer was washed with brine, dried over Na$_2$SO$_4$, and concentrated to give, after purification of the crude product by MPLC or recrystallization, the desired 1-(pyrazol-3-yl)-1-propyn-3-ol. Analytical data, for select compounds of this type appear in Tables E & F

TABLE E

| Cpd | R$_1$ | R$_5$ | mp, ° C. | MS, [M + H]+ |
|---|---|---|---|---|
| 58 | Me | H | 150–151 | 319 |
| 59 | Me | Me | 60–70 dec | 333 |
| 60 | Me | Et | 135–137 | 347 |
| 61 | Me | i-Pr | 157–159 | 361 |
| 62 | Et | Me | foam | 347 |
| 63 | Cl | H | 132–134 | 339 |
| 64 | Cl | Me | 127–128 | 353 |
| 65 | Cl | Et | 128–129 | 367 |
| 66 | Cl | i-Pr | oil | 381 |

TABLE F

| | | Calcd | | | Found | | |
|---|---|---|---|---|---|---|---|
| Cpd | Empirical formula | | C | H | N | C | H | N |
| 58 | C$_{20}$H$_{18}$N$_2$O$_2$ 0.25 H$_2$O | 74.4 | 5.78 | 8.68 | 74.26 | 5.58 | 8.70 |
| 59 | C$_{21}$H$_{20}$N$_2$O$_2$ | 75.88 | 6.06 | 8.43 | 75.56 | 6.02 | 8.07 |
| 60 | C$_{22}$H$_{22}$N$_2$O$_2$ | 76.28 | 6.40 | 8.09 | 76.12 | 6.38 | 8.08 |

TABLE F-continued

| Cpd | Empirical formula | | Calcd C | H | N | Found C | H | N |
|---|---|---|---|---|---|---|---|---|
| 61 | $C_{23}H_{24}N_2O_2$ | | 76.64 | 6.71 | 7.77 | 76.57 | 6.62 | 7.75 |
| 63 | $C_{19}H_{15}ClN_2O_2$ | 0.25 $H_2O$ | 66.48 | 4.55 | 8.16 | 66.53 | 4.66 | 7.93 |
| 64 | $C_{20}H_{17}ClN_2O_2$ | 0.65 $H_2O$ | 65.9 | 5.06 | 7.68 | 65.94 | 4.96 | 7.29 |
| 65 | $C_{21}H_{19}ClN_2O_2$ | 0.1 $H_2O$ | 68.42 | 5.25 | 7.60 | 68.38 | 5.56 | 7.20 |
| 66 | $C_{22}HClN_2O_2$ | 0.3 $C_4H_{10}O$ | 69.13 | 6.00 | 6.95 | 69.06 | 6.19 | 6.56 |

Example 11

N,O-Bis(phenoxycarbonyl)-N-{1-[1-(4-methoxyphenyl)-5-(4-methylphenyl)-3-pyrazolyl]-1-propyn-3-yl}hydroxylamine (Cpd. 67). A solution of diethyl azodicarboxylate (16.6 mmol, 2.89 g, 2.61 mL) in 20 mL of THF was added dropwise under $N_2$ to a stirring solution of Cpd. 58 (13.3 mmol, 4.23 g), triphenylphosphine (16.6 mmol, 4.35 g), and N,O-bis(phenoxycarbonyl)hydroxylamine (15.9 mmol, 4.34 g) in 40 mL of THF at 0° C. The reaction mixture was stirred at 0° C. for 1 h and room temperature for 1.5 h. Solvent was removed using a rotary evaporator and the sticky residue was purified directly by MPLC using a solvent gradient ranging from 60% $CH_2Cl_2$/hexanes to 100% $CH_2Cl_2$ to yield 3.79 g (50%) of Cpd. 67 as a yellow foam; $^1$H NMR (CDCl$_3$, 300 MHz) 2.35 (s, 3H), 3.82 (s, 3H), 4.89 (s, 2H), 6.61 (s, 1H), 6.85 (d, 2H, J=9), 7.12 (m, 4H), 7.2–7.5 (complex, 12H). In addition, 2.13 g (35%) of N-phenoxycarbonyl-N-(1-(1-(4-methoxyphenyl)-5-(4-methylphenyl)-3-pyrazolyl)-1-propyn-3-yl)hydroxylamine was isolated from the more polar fractions; $^1$H NMR (CDCl$_3$, 300 MHz) 2.34 (s, 3H), 3.80 (s, 3H), 4.70 (s, 2H), 6.56 (s, 1H) , 6.85 (d, 2H, J=9) , 7.07 (m, 4H) , 7.2–7.4 (complex, 7H).

Example 12

N,O-Bis(t-butoxycarbonyl)-N-(1-(1-(4-methoxyphenyl)-5-(4-methylphenyl)-3-pyrazolyl]-1-butyn-3-yl)hydroxylamine (Cpd. 76). Diethyl azodicarboxylate (3.30 mmol, 0.575 g, 0.520 mL) was added dropwise under $N_2$ to a stirring solution of Cpd. 59 (2.97 mmol, 0.987 g), triphenylphosphine (3.30 mmol, 0.867 g), and N,O-bis(t-butoxycarbonyl)hydroxylamine (3.30 mmol, 0.770 g) in 9 mL of THF at –20° C. (measured externally in a $CCl_4$/dry ice bath). The reaction mixture was stirred at room temperature for overnight, and solvent was removed using a rotary evaporator. The sticky residue was dissolved in ether, hexanes was added, and the resulting precipitate was filtered and washed with more hexanes. The combined filtrates were concentrated and purified by MPLC using a solvent gradient ranging from 20–25% EtOAc/hexanes to give 1.01 g (62%) of Cpd. 76 as a white foam; $^1$H NMR (CDCl$_3$, 300 MHz) 1.51 (s, 9H), 1.53 (s, 9H), 1.54 (obscured d, 3H), 2.34 (s, 3H), 3.81 (s, 3H), 5.24 (broad s, 1H), 6.53 (broad s, 1H), 6.83 (d, 2H, J=9), 7.08 (m, 4H), 7.18 (d, 2H, J=9); IR (KBr) 1790, 1719, 1515, 1258, 1165 cm$^{-1}$; MS (FAB) m/z 548, 315 (base). Anal. Calcd for $C_{31}H_{37}N_3O_6$: C, 67.99; H, 6.81; N, 7.67. Found: C, 67.96; H, 6.88; N, 7.59.

Example 13

General procedure for the preparation of substituted N,O-bis(t-butoxycarbonyl)-N-(1-(pyrazol-3-yl)-1-propyn-3-yl) hydroxylamines or substituted N,O-bis(phenoxycarbonyl)-N-(1-(pyrazol-3-yl)-1-propyn-3-yl)hydroxylamines. A solution of diethylazodicarboxylate (12.5 mmol) in 15 mL of THF was added dropwise under $N_2$ to a stirring solution of the appropriately substituted 1-(pyrazol-3-yl)-1-propyn-3-ol (10 mmol), triphenylphosphine, 12.5 mmol), and either N,O-(bis-t-butoxycarbonyl)hydroxylamine (12 mmol) or N,O-(bis-phenoxycarbonyl)hydroxylamine (12 mmol) in 25 mL of THF at 0° C. The reaction mixture was stirred at 0° C. for 1–2 h and at room temperature for 1–24 h. Solvent was removed using a rotary evaporator and the residue was purified by MPLC to give the desired N,O-(bis-t-butoxycarbonyl)-N-(1-(pyrazol-3-yl)-1-propyn-3-yl) hydroxylamine or N,O-(bis-phenoxycarbonyl)-N-(1-(pyrazol-3-yl)-1-propyn-3-yl)hydroxylamine.

TABLE G

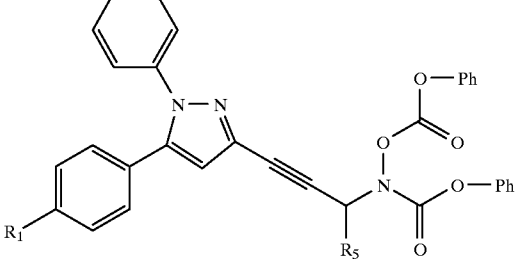

| Cpd | $R_1$ | $R_5$ | mp, ° C. | characterization |
|---|---|---|---|---|
| 67 | Me | H | foam | $^1$H NMR |
| 68 | Me | Me | foam | $^1$H NMR |
| 69 | Me | Et | foam | $^1$H NMR |
| 70 | Me | i-Pr | oil | $^1$H NMR |
| 71 | Cl | H | oil | $^1$H NMR |
| 72 | Cl | Me | foam | $^1$H NMR |
| 73 | Cl | Et | oil | $^1$H NMR |
| 74 | Cl | i-Pr | foam | $^1$H NMR |

TABLE H

| Cpd | R₁ | R₅ | mp, °C. | MS, [M + H]+ |
|---|---|---|---|---|
| 75 | Me | H | foam | 534 |
| 76 | Me | Me | foam | 548 |
| 77 | Me | Et | foam | 562 |
| 78 | Et | Me | foam | 562 |
| 79 | Cl | Me | 105–110 | 569 |

Example 14

N-Hydroxy-N-(1(1-(4-methoxyphenyl)-5-(4-methylphenyl)pyrazol-3-yl)-1-propyn-3-yl)urea (Cpd. 1). Compound 63 (6.59 mmol, 3.78 g) was dissolved in 30 mL of 14% w/w solution of ammonia in MeOH and stirred in a stoppered round-bottomed flask (with the 24/40 glass stopper sealed with Teflon tape and clamped to the flask) for 4 h. The flask was carefully vented and an additional 15 mL of methanolic ammonia was added. After 2 h, the solution was concentrated to give 4 g of orange oil which was purified by MPLC using a solvent gradient ranging from 75% EtOAc/hexanes to 100% EtOAc to provide 1.51 g (61%) of Cpd. 1 as an off-white solid, m.p. 108–112° C. (dec); $^1$H NMR (DMSO-$d_6$, 300 MHz) 2.28 (s, 3H), 3.78 (s, 3H), 4.34 (s, 2H), 6.56 (s, 2H), 6.73 (s, 1H) 6.96 (d, 2H, J=9), 7.05–7.25 (complex, 7H), 9.61 (s, 1H); IR (KBr) 3150, 1655, 1515, 1252, 835 cm$^{-1}$; MS (DCI) m/z 377, 360, 346, 334, 317 (base), 301, 289. Anal. Calcd for $C_{21}H_{20}N_4O_3$.0.5 $H_2O$: C, 65.44; H, 5.49; N, 14.54. Found: C, 65.63; H, 5.29; N, 14.35.

Alternatively, N-phenoxycarbonyl-N-(1(1-(4-methoxyphenyl)-5-(4-methylphenyl)-3-pyrazolyl)-1-propyn-3-yl)hydroxylamine (4.67 mmol, 2.12 g) was dissolved in 20 mL of 14% w/w solution of ammonia in MeOH and stirred overnight in a stoppered round-bottomed flask. The solution was concentrated to give 2.2 g of orange oil which was purified by MPLC to give 0.89 g (51%) of Cpd. 1 as an off white solid. Tables I & J list the analytical data for Cpd. 1 as well as other compounds which were prepared in this manner.

TABLE I

| Cpd | R₁ | R₅ | R₉ | R₁₀ | mp, °C. | MS, [M + H]+ |
|---|---|---|---|---|---|---|
| 1 | Me | H | H | H | 108–112 dec | 377 |
| 2 | Me | Me | H | H | 110–120 dec | 391 |
| 3 | Me | Et | H | H | 90–100 dec | 405 |
| 4 | Me | i-Pr | H | H | 185–187 dec | 419 |
| 5 | Cl | H | H | H | 113–120 dec | 397 |
| 6 | Cl | Me | H | H | 163–165 | 411 |
| 7 | Cl | Me | H | Me | 182–183 | 425 |
| 8 | Cl | Me | H | n-Pr | 85–90 | 453 |
| 9 | Cl | Me | (CH₂)₅ | | 75–80 | 479 |
| 10 | Cl | Me | (CH₂)₂O(CH₂)₂ | | 153–155 | 481 |
| 11 | Cl | Et | H | H | foam | 425 |
| 12 | Cl | i-Pr | H | H | 162–164 | 439 |

TABLE J

| | | Calcd | | | Found | | |
|---|---|---|---|---|---|---|---|
| Cpd | Empirical formula | | C | H | N | C | H | N |
|---|---|---|---|---|---|---|---|---|
| 1 | $C_{21}H_{20}N_4O_3$ | 0.5 $H_2O$ | 65.44 | 5.49 | 14.54 | 65.63 | 5.29 | 14.35 |
| 2 | $C_{22}H_{22}N_4O_3$ | 0.45 $H_2O$ | 66.30 | 5.79 | 14.06 | 66.57 | 5.61 | 13.71 |
| 3 | $C_{23}H_{24}N_4O_3$ | 0.4 $H_2O$ | 67.10 | 6.07 | 13.61 | 67.36 | 6.17 | 13.35 |
| 4 | $C_{24}H_{26}N_4O_3$ | | 68.88 | 6.26 | 13.39 | 68.71 | 6.42 | 13.23 |
| 5 | $C_{20}H_{17}ClN_4O_3$ | 0.25 $C_4H_8O_2$ | 60.22 | 4.57 | 13.38 | 59.95 | 4.36 | 13.53 |
| 6 | $C_{21}H_{19}ClN_4O_3$ | 0.3 $C_4H_8O_2$ | 60.98 | 4.93 | 12.81 | 60.60 | 4.67 | 13.04 |
| 7 | $C_{22}H_{21}ClN_4O_3$ | 0.4 $H_2O$ | 61.15 | 5.09 | 12.97 | 61.35 | 5.03 | 12.74 |
| 8 | $C_{24}H_{25}ClN_4O_3$ | 0.25 $C_4H_8O_2$ | 63.22 | 5.73 | 11.80 | 62.86 | 5.61 | 11.7 |
| 9 | $C_{26}H_{27}ClN_4O_3$ | 0.35 $C_4H_8O_2$ | 64.55 | 5.89 | 10.99 | 64.22 | 5.70 | 11.04 |
| 10 | $C_{25}H_{25}ClN_4O_4$ | 0.25 $C_4H_8O_2$ | 62.09 | 5.41 | 11.14 | 61.75 | 5.48 | 10.89 |
| 11 | $C_{22}H_{21}ClN_4O_3$ | 0.5 $C_4H_8O_2$ | 61.47 | 5.37 | 11.95 | 61.67 | 5.22 | 11.71 |
| 12 | $C_{23}H_{23}ClN_4O_3$ | 0.35 $CH_4N_2O$ 0.5 $H_2O$ | 59.81 | 5.46 | 14.04 | 59.86 | 5.36 | 13.92 |

Example 15

N-(1-(1-(4-methoxyphenyl)-5-(4-methylphenyl)pyrazol-3-yl)-1-butyn-3-yl)hydroxylamine (Cpd. 81). A solution of Cpd. 76 (1.73 mmol, 0.950 g) was dissolved in 5 mL of trifluoroacetic acid (TFA) and was stirrred under $N_2$ overnight. The mixture was concentrated and the oily residue was partitioned between ether and saturated aqueous $Na_2CO_3$. After drying over $Na_2SO_4$, the solution was concentrated to give 0.634 g (~100%) of Cpd. 81 as a yellow foam; $^1$H NMR (CDCl$_3$, 300 MHz) 1.45 (d, 3H, J=7), 2.33 (s, 3H), 3.81 (s, 3H), 6.56 (s, 1H), 6.83 (d, 1H, J=9), 7.08 (m, 4H), 7.20 (d, 1H, J=2H); MS (DCI) m/z 348, 330, 315 (base), 289.

Example 16

General procedure for the preparation of substituted N-(1-(pyrazol-3-yl)-1-propyn-3-yl)hydroxylamines. A solution of the appropriately substituted N,O-bis(t-butoxycarbonyl)-N-(1-(pyrazol-3-yl)-1-propyn-3-yl)hydroxylamine (10 mmol) was dissolved in 20–30 mL of TFA or a mixture of TFA and $CH_2Cl_2$ and was stirred under $N_2$ for 4–24 h. The mixture was concentrated and the residue was partitioned between saturated aqueous $Na_2CO_3$ and ether or EtOAc. The organic extracts were dried over $Na_2SO_4$ and concentrated to provide the desired substituted N-(1-(pyrazol-3-yl)-1-propyn-3-yl)hydroxylamine. The analytical data for some of the compounds prepared by this method are listed in Table K

TABLE K

| Cpd | $R_1$ | $R_5$ | mp, °C. | MS, [M + H]+ |
|---|---|---|---|---|
| 80 | Me | H | foam | 334 |
| 81 | Me | Me | foam | 348 |
| 82 | Me | Et | oil | 362 |
| 83 | Et | Me | 64–65 | 362 |
| 84 | Cl | Me | foam | 368 |

Example 17

N,O-Bis(acetyl)-N-(1-(1-(4-methoxyphenyl)-5-(4-methylphenyl)pyrazol-3-yl)-1-butyn-3-yl)hydroxylamine (Cpd. 85). Acetyl chloride (4.50 mmol, 0.353 g, 0.320 mL) was added dropwise under $N_2$ to a solution of Cpd. 81 (1.80 mmol, 0.625 g) and pyridine (5.40 mmol, 0,427 g, 0.437 mL) in 6 mL of $CH_2Cl_2$ at room temperature. After stirring at room temperature under $N_2$ overnight, 20 mL of aqueous 1N HCl was added and the mixture was extracted with ether. The organic layer was washed with water, saturated aqueous $NaHCO_3$, and brine and was dried over $Na_2SO_4$ to give, after concentration, 0.826 g of brown oil. The crude product was purified by MPLC using 1:2 EtOAc/hexanes to afford 0.711 g (92%) of Cpd. 85 as a white foam; $^1$H NMR (CDCl$_3$, 300 MHz) 1.52 (d, 3H, J=7), 2.07 (s, 3H), 2.28 (s, 3H), 2.34 (s, 3H), 3.81 (s, 3H), 5.64 (broad s, 1H), 6.54 (s, 1H), 6.83 (d, 2H, J=9), 7.08 (m, 4), 7.19 (d, 2H, J=9); IR (KBr) 1800, 1682, 1515, 1250, 1179 cm$^{-1}$; MS (DCI) m/z 432 (base), 389, 372, 330, 315. Anal. Calcd for $C_{25}H_{25}N_3O_4$·0.2 $C_4H_8O_2$: C, 69.00; H, 5.97; N, 9.36. Found: C, 69.02; H, 5.90; N, 9.35.

Example 18

General procedure for the preparation of substituted N,O-bis(acyl)-N-(1-(pyrazol-3-yl)-1-propyn-3-yl) hydroxylamines. The appropriate acid chloride (2.5 mmol) was added dropwise under $N_2$ to a solution of the appropriately substituted N-(1-(pyrazol-3-yl)-1-butyn-3-yl) hydroxylamine (1.0 mmol) and pyridine (3.0 mol) in 4–5 mL of $CH_2Cl_2$ at 0° C. or room temperature. After stirring at room temperature for 4–24 h, 10 mL of aqueous 1N HCl was added and the mixture was extracted with ether or EtOAc. The organic layer was washed with water, saturated aqueous $NaHCO_3$, and brine, dried over $Na_2SO_4$, and concentrated ot give a crude product which was purified by MPLC to give the desired N,O-bis(acyl)-N-(1-(pyrazol-3-yl)-1-propyn-3-yl)hydroxylamine.

TABLE L

| Cpd | $R_1$ | $R_5$ | $R^a$ | mp, °C. | MS, [M + H]+ |
|---|---|---|---|---|---|
| 85 | Me | Me | Me | foam | 432 |
| 86 | Me | Me | Et | <50 | 460 |
| 87 | Me | Me | i-Pr | <50 | 488 |
| 88 | Me | Me | $CH_2CH_2CO_2Et$ | foam | 604 |
| 89 | Me | Me | 2-furyl | foam | 536 |
| 90 | Me | Me | Ome | 51–59 | 465 |
| 91 | Cl | Me | Me | 90–100 | 452 |
| 92 | Cl | Me | Et | 68–70 | 480 |
| 93 | Cl | Me | i-Pr | 50–55 | 509 |
| 94 | Cl | Me | n-$C_7H_{15}$ | oil | 621 |
| 95 | Cl | Me | Ph | foam | 577 |
| 96 | Cl | Me | Ome | 85–90 | 484 |

TABLE M

| Cpd | Empirical formula | | Calcd | | | Found | | |
|---|---|---|---|---|---|---|---|---|
| | | | C | H | N | C | H | N |
| 85 | $C_{25}H_{25}N_3O_4$ | 0.2 $C_4H_8O_2$ | 69.00 | 5.97 | 9.36 | 69.02 | 5.90 | 9.35 |
| 86 | $C_{27}H_{29}N_3O_4$ | | 70.57 | 6.36 | 9.14 | 70.48 | 6.49 | 8.90 |
| 87 | $C_{29}H_{33}N_3O_4$ | | 71.44 | 6.82 | 8.62 | 71.38 | 6.87 | 8.40 |
| 89 | $C_{31}H_{25}N_3O_6$ | | 69.52 | 4.71 | 7.85 | 69.18 | 4.66 | 7.59 |

TABLE M-continued

| | | Calcd | | | Found | | |
|---|---|---|---|---|---|---|---|
| Cpd | Empirical formula | C | H | N | C | H | N |
| 90 | $C_{25}H_{25}N_3O_6$ | 64.79 | 5.44 | 9.07 | 64.79 | 5.48 | 8.78 |
| 91 | $C_{24}H_{22}ClN_3O_4$ | 63.79 | 4.91 | 9.30 | 63.67 | 4.90 | 8.99 |
| 92 | $C_{26}H_{26}ClN_3O_4$ | 65.06 | 5.46 | 8.75 | 64.84 | 5.49 | 8.50 |
| 93 | $C_{28}H_{30}ClN_3O_4$ | 66.20 | 5.95 | 8.27 | 66.10 | 5.97 | 8.04 |
| 94 | $C_{36}H_{46}ClN_3O_4$ 0.5 $C_8H_{16}O_2$ | 69.39 | 7.86 | 6.07 | 69.52 | 7.62 | 6.21 |
| 95 | $C_{34}H_{26}ClN_3O_4$ | 70.89 | 4.55 | 7.29 | 70.71 | 4.55 | 7.13 |
| 96 | $C_{24}H_{22}ClN_3O_6$ | 59.57 | 4.58 | 8.68 | 59.48 | 4.60 | 8.49 |

Example 19

N-Acetyl-N-(1-(1-(4-methoxyphenyl)-5-(4-methylphenyl)pyrazol-3-yl)-1-butyn-3-yl)hydroxylamine (Cpd. 18). A solution of Cpd. 85 (1.24 mmol, 0.535 g) in 6 mL of MeOH was treated with 0.25 mL (~4 mmol) of concentrated aqueous $NH_4OH$ and was stirred under $N_2$ overnight. The mixture was concentrated to give 0.515 g of crude product which was purified by MPLC using a solvent gradient ranging from 50–66% EtOAc/hexanes to give pure Cpd. 18 as a colorless oil. The oil was converted into a white foam by evaporation from ether and pumping at high vacuum to give 0.457 g (90%) of Cpd 18 as an ether solvate; $^1$H NMR (DMSO-$d_6$, 300 MHz) 1.41 (d, 3H, J=7), 2.04 (s, 3H), 2.28 (s, 3H), 3.78 (s, 3H), 5.51 (q, 1H, J=7), 6.75 (s, 1H), 6.96 (d, 2H, J=9), 7.05–7.25 (complex, 6H), 9.93 (broad s, 1H); IR (KBr) 3100 (broad), 1660, 1614, 1515, 1444, 1416, 1251 $cm^{-1}$; MS (DCI) m/z 390, 332 (base), 315. Anal. Calcd for $C_{23}H_{23}N_3O_3 \cdot 0.25\ C_4H_{10}O$: C, 70.66; H, 6.30; N, 10.30. Found: C, 70.35; H, 6.01; N, 10.47.

Example 20

N-Chloroacetyl-N-(1-(1-(4-methoxyphenyl)-5-(4-methylphenyl)pyrazol-3-yl)-1-butyn-3-yl)hydroxylamine (Cpd. 21). Chloroacetyl chloride (3.76 mmol, 0.425 g, 0.30 mL) was added dropwise under $N_2$ to a solution of Cpd. 81 (1.88 mmol, 0.72 g) and imidazole (5.64 mmol, 0.38 g) in 10 mL of $CH_2Cl_2$ at 0° C. The mixture was stirred at room temperature for 3 days and was partitioned between water and $CH_2Cl_2$. The organic layer was washed with brine, dried over $Na_2SO_4$, and concentrated to give a crude product which was purified by MPLC using 50% EtOAc/hexanes to give 0.54 g (68%) of Cpd. 21 as a white foam; $^1$H NMR (DMSO-$d_6$, 300 MHz) 1.45 (d, 3H, J=7), 2.28 (s, 3H), 3.77 (s, 3H), 4.46 (s, 2H), 5.49 (q, 1H, J=7), 6.77 (s, 1H), 6.96 (d, 2H, J=9), 7.05–7.25 (complex, 6H), 10.23 (broad s, 1H); IR (KBr): 3125 (broad), 1692, 1518, 1252 $cm^{-1}$; MS (DCI): 424, 408, 374, 333, 315 (base). Anal. Calcd for $C_{23}H_{22}ClN_3O_3$: C, 65.17; H, 5.23; N, 9.91. Found: C, 65.03; H, 5.21; N, 9.74.

Example 21

General procedure for the preparation of substituted N-acyl-N-(1-(pyrazol-3-yl)-1-propyn-3-yl)hydroxylamines. Method A. A solution of the appropriately substituted N,O-bis(acyl)-N-(1-(pyrazol-3-yl)-1-propyn-3-yl)hydroxylamine (1.0 mmol) in 5 mL of MeOH was treated with 0.20 mL (~3 mmol) of concentrated aqueous $NH_4OH$ and was stirred under $N_2$ overnight. The mixture was concentrated to give a crude product which was purified by MPLC or recrystallization to give the desired N-acyl-N-(1-(pyrazol-3-yl)-1-propyn-3-yl)hydroxylamine. Alternatively, a solution of the appropriately substituted N,O-bis(acyl)-N-(1-(pyrazol-3-yl)-1-propyn-3-yl)hydroxylamine (1.0 mmol) in 5–10 mL of MeOH was treated with 3–5 mL 1N aqueous NaOH. After stirring at room temperature overnight, the mixture was acidified to pH 7–8 with 1N aqueous HCl and was partitioned between water and ether or EtOAc, The organic layer was washed with brine, dried over $Na_2SO_4$, and concentrated to give a crude product which was purified by MPLC or recrystallization to give the desired N-acyl-N-(1-(pyrazol-3-yl)-1-propyn-3-yl)hydroxylamine. Method B. A solution of the appropriately substituted N-(1-(pyrazol-3-yl)-1-propyn-3-yl)hydroxylamine (1.0 mmol) in 5–10 mL of ether or $CH_2Cl_2$ was combined with 5–6 mL of 1N aqueous $Na_2CO_3$ or 1N aqueous NaOH and stirred rapidly while the appropriate acid chloride or anhydride (1.5–2 mmol) was added dropwise. The mixture was stirred at room temperature for 4–24 h and was partitioned between ether or EtOAc. The organic layer was washed with water and brine, dried over $Na_2SO_4$ or $MgSO_4$, and concentrated to give a crude product which was purified by MPLC or recrystallization to give the desired N-acyl-N-(1-(pyrazol-3-yl)-1-propyn-3-yl) hydroxylamine. Alternatively, the appropriate acid chloride (1.2–1.5 mmol)was added dropwise under $N_2$ to a solution of the appropriately substituted N-(1-(pyrazol-3-yl)-1-propyn-3-yl)hydroxylamine (1.0 mmol) and pyridine (2 mmol) in 5 mL of $CH_2Cl_2$ at 0° C. The solution was stirred at room temperature for 1–2 days and was partitioned between water and $CH_2Cl_2$. The organic layer was washed with brine, dried over $Na_2SO4$, and concentrated to give a crude product which was purified by MPLC or recrystallization to give the desired N-chloroacetyl-N-(1-pyrazol-3-yl)-1-propyn-3-yl)hydroxylamine.

TABLE N

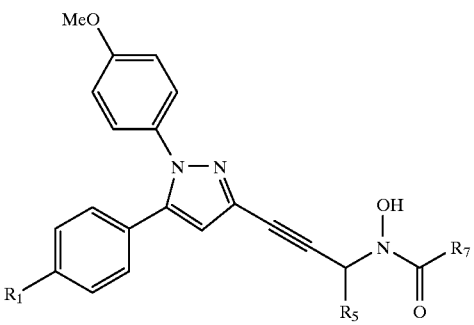

| Cpd | $R_1$ | $R_5$ | $R_7$ | mp, ° C. | MS, [M + H]+ | Method |
|---|---|---|---|---|---|---|
| 13 | Me | H | Me | 144–146 | 376 | B |
| 14 | Me | H | Et | 138 | 390 | B |
| 15 | Me | H | Ph | foam | 438 | B |
| 16 | Me | H | 4-pyridyl | 75–90 | 439 | B |
| 17 | Me | H | Ome | 138 | 392 | B |
| 18 | Me | Me | Me | foam | 390 | A |
| 19 | Me | Me | Et | foam | 404 | A |
| 20 | Me | Me | i-Pr | foam | 418 | A |

TABLE N-continued

[Structure: pyrazole with MeO-phenyl on N1, R1-phenyl on C5, and C3 substituted with -C≡C-CH(R5)-N(OH)-C(=O)-R7]

| Cpd | R₁ | R₅ | R₇ | mp, °C. | MS, [M + H]+ | Method |
|---|---|---|---|---|---|---|
| 21 | Me | Me | CH₂Cl | foam | 424 | B |
| 22 | Me | Me | CH₂CH₂CO₂Et | foam | 476 | A |
| 23 | Me | Me | CF₃ | 142–144 | 444 | B |
| 24 | Me | Me | CO₂Et | foam | 448 | B |
| 25 | Me | Me | 2-furyl | 148–150 | 442 | A |
| 26 | Me | Me | 3-pyridyl | 114–116 | 453 | B |
| 27 | Me | Me | Ome | foam | 406 | A |
| 28 | Me | Et | Me | foam | 404 | A |
| 29 | Et | Me | Me | 61–76 | 404 | B |
| 30 | Et | Me | i-Pr | 63–72 | 432 | B |
| 31 | Et | Me | CH₂Cl | 157 | 438 | B |
| 32 | Et | Me | CH₂CH₂CO₂Et | <50 | 490 | B |
| 33 | Et | Me | CH₂CH₂CO₂H | 134–137 | 462 | * |
| 34 | Et | Me | Ome | foam | 420 | B |
| 35 | Cl | Me | Me | 168–169 | 410 | A |
| 36 | Cl | Me | Et | 169–170 | 424 | A |
| 37 | Cl | Me | i-Pr | 101–103 | 438 | A |
| 38 | Cl | Me | n-C₇H₁₅ | 128–129 | 495 | A |
| 39 | Cl | Me | CH₂CH₂CO₂H | foam | 468 | B |
| 40 | Cl | Me | Ph | 183–184 | 472 | A |
| 41 | Cl | Me | Ome | 163–164 | 426 | A |

*by saponification of CP 30.

TABLE O

| Cpd | Empirical formula | | Calcd C | H | N | Found C | H | N |
|---|---|---|---|---|---|---|---|---|
| 13 | C₂₂H₂₁N₃O₃ | 0.1 C₄H₈O₂ | 70.02 | 5.72 | 10.94 | 69.96 | 5.68 | 11.01 |
| 14 | C₂₃H₂₃N₃O₃ | | 70.93 | 5.95 | 10.79 | 70.92 | 5.87 | 10.72 |
| 15 | C₂₇H₂₃N₃O₃ | 0.3 C₄H₈O₂ | 73.01 | 5.52 | 9.06 | 73.04 | 5.36 | 9.31 |
| 16 | C₂₆H₂₂N₄O₃ | 0.1 H₂O 0.4 C₄H₈O₂ | 69.71 | 5.38 | 11.78 | 69.79 | 5.29 | 11.86 |
| 17 | C₂₂H₂₁N₃O₄ | | 67.51 | 5.41 | 10.74 | 67.52 | 5.38 | 10.65 |
| 18 | C₂₃H₂₃N₃O₃ | 0.25 C₄H₁₀O | 70.66 | 6.30 | 10.30 | 70.35 | 6.01 | 10.47 |
| 19 | C₂₄H₂₅N₃O₃ | | 71.44 | 6.25 | 10.41 | 71.14 | 6.33 | 10.09 |
| 20 | C₂₅H₂₇N₃O₃ | | 71.92 | 6.52 | 10.06 | 71.86 | 6.43 | 10.00 |
| 21 | C₂₃H₂₂ClN₃O₃ | | 65.17 | 5.23 | 9.91 | 65.03 | 5.21 | 9.74 |
| 22 | C₂₇H₂₉N₃O₅ | | 68.19 | 6.15 | 8.84 | 68.08 | 6.20 | 8.57 |
| 23 | C₂₃H₂₀F₃N₃O₃ | | 62.30 | 4.55 | 9.48 | 62.33 | 4.48 | 9.40 |
| 24 | C₂₅H₂₅N₃O₅ | 0.3 C₄H₁₀O | 66.63 | 5.76 | 9.03 | 66.64 | 5.69 | 9.13 |
| 25 | C₂₆H₂₃N₃O₄ | 0.3 H₂O | 69.88 | 5.32 | 9.40 | 69.85 | 5.24 | 9.39 |
| 26 | C₂₇H₂₄N₄O₃ | 0.4 C₄H₈O₂ | 70.43 | 5.62 | 11.49 | 70.59 | 5.76 | 11.34 |
| 27 | C₂₃H₂₃N₃O₄ | | 68.13 | 5.72 | 10.36 | 67.79 | 5.80 | 10.09 |
| 28 | C₂₄H₂₅N₃O₃ | 0.1 H2O | 71.13 | 6.27 | 10.37 | 70.99 | 6.26 | 10.18 |
| 29 | C₂₄H₂₅N₃O₃ | | 71.44 | 6.25 | 10.41 | 71.25 | 6.26 | 10.09 |
| 30 | C₂₈H₂₉N₃O₃ | 0.20 C₄H₈O₂ | 71.67 | 6.87 | 9.36 | 71.66 | 6.80 | 9.58 |
| 31 | C₂₄H₂₄ClN₃O₃ | | 65.83 | 5.52 | 9.60 | 65.45 | 5.47 | 9.42 |
| 32 | C₂₈H₃₁N₃O₅ | | 68.69 | 6.38 | 8.58 | 68.42 | 6.36 | 8.45 |
| 33 | C₂₆H₂₇N₃O₅ | | 67.67 | 5.90 | 9.10 | 67.45 | 5.96 | 8.88 |
| 34 | C₂₄H₂₅N₃O₄ | | 68.72 | 6.01 | 10.02 | 68.32 | 6.04 | 9.85 |
| 35 | C₂₂H₂₀ClN₃O₃ | 0.3 SiO₂ | 61.75 | 4.68 | 9.82 | 61.68 | 4.62 | 9.71 |
| 36 | C₂₃H₂₂ClN₃O₃ | | 65.17 | 5.23 | 9.91 | 64.86 | 5.16 | 9.72 |
| 37 | C₂₄H₂₃ClN₃O₃ | | 65.82 | 5.52 | 9.60 | 65.62 | 5.60 | 9.45 |
| 38 | C₂₈H₃₂ClN₃O₃ | | 68.07 | 6.53 | 8.51 | 67.86 | 6.52 | 8.40 |
| 39 | C₂₄H₂₂ClN₃O₅ | 0.1 H₂O | 61.37 | 4.76 | 8.95 | 61.02 | 4.90 | 8.56 |
| 40 | C₂₇H₂₂ClN₃O₃ | | 68.72 | 4.70 | 8.90 | 68.66 | 4.73 | 8.64 |
| 41 | C₂₂H₂₀ClN₃O₄ | | 62.05 | 4.73 | 9.87 | 61.8 | 4.77 | 9.60 |

Example 22

N-(4-methylpiperazin-1-yl)acetyl-N-(1-[5-(4-ethylphenyl)-1-(4-methoxyphenyl)pyrazol-3-yl]-1-butyn-3-yl)hydroxylamine (Cpd. 45). A solution of Cpd. 31 (0.71 mmol, 0.31 g) in 4 mL of DMF was stirred with 4-methylpiperazine (3.55 mmol, 0.36 g, 0.40 mL), under N₂ overnight. The reaction mixture was partitioned between water and EtOAc; the organic layer was washed several times with water, dried over MgSO$_4$, and concentrated to give 0.25 g (70%) of Cpd. 45 (free base) as a white foam. An analytical sample was prepared by adding oxalic acid to an acetone solution of Cpd. 45 to give 0.128 g of a white solid, m.p. 150° C.; $^1$H NMR (DMSO-d6, 300 MHz) 1.15 (t, 3H, J=7.5), 1.43 (d, 3H, J=7), 3.04 (q, 2H, J=7.5), 2.72 (s, 3H), 2.80 (m, 4H), 3.15 (m, 4H), 3.49 (s, 2H), 3.7–4.8 (broad s, >5H), 3.78 (s, 3H), 5.48 (q, 1H, J=7), 6.75 (s, 1H), 6.97 (d, 2H, J=9), 7.05–7.25 (complex, 6H); IR (KBr) 3400 (broad), 2700 (broad), 1725, 1663, 1618, 1515, 1251 cm$^{-1}$; MS (DCI) m/z 502, 486, 329, 159, 113 (base). Anal. Calcd for C$_{29}$H$_{35}$N$_5$O$_3$ 1.75 C$_2$H$_2$O$_4$: C, 59.22; H, 5.89; N, 10.62. Found: C, 59.49; H, 6.18; N, 10.34.

Example 23

General procedure for the preparation of substituted N-aminoacetyl-N-(1-(pyrazol-3-yl)-1-propyn-3-yl) hydroxylamines. A solution of the appropriately substituted N-chloroacetyl-N-(1-(pyrazol-3-yl)-1-propyn-3-yl) hydroxylamine (1.0 mmol) in 5 mL of DMF was stirred with the appropriate primary or secondary amine (5.0 mmol), under N$_2$ overnight. The reaction mixture was partitioned between water and EtOAc; the organic layer was washed several times with water, dried over MgSO$_4$ or Na$_2$SO$_4$, and concentrated to give the desired N-aminoacetyl-N-(1-(pyrazol-3-yl)-1-propyn-3-yl)hydroxylamine which was isolated as its oxalate salt.

TABLE P

| Cpd | R$_1$ | R$_5$ | R$_7$ | mp, ° C. | MS, [M + H]+ |
|---|---|---|---|---|---|
| 42 | Me | Me | CH$_2$NH(CH$_2$)$_3$NMe$_2$ | 175–177 | 490 |
| 43 | Me | Me | CH$_2$-imidazol-1-yl | 125–130 | 456 |
| 44 | Et | Me | CH$_2$-morpholin-4-yl | 183 | 489 |
| 45 | Et | Me | CH$_2$-4-methyl-piperazin-1-yl | 150 | 502 |

What is claimed is:
1. A compound of the Formula I

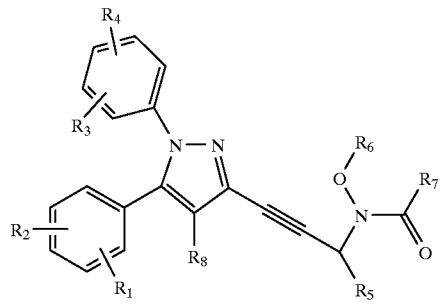

wherein:
R$_1$, R$_2$, R$_3$, and R$_4$ are independently selected from the groups consisting of hydrogen, C$_{1-5}$alkyl, C$_{1-5}$alkoxy, phenyl, halo, hydroxy, C$_{1-5}$alkylsulfonyl, C$_{1-5}$alkylthio, trihaloC$_{1-5}$alkyl, amino, nitro and 2-quinolinylmethoxy; R$_5$ is hydrogen, C$_{1-5}$alkyl, trihaloC$_{1-5}$alkyl, phenyl, substituted phenyl where the phenyl substitutents are halogen, C$_{1-5}$alkoxy, trihaloC$_{1-5}$alkyl or nitro or R$_5$ is heteroaryl of 5–7 ring members where at least one of the ring members is nitrogen, sulfur or oxygen; R$_6$ is hydrogen, C$_{1-5}$alkyl, phenyl C$_{1-5}$alkyl, substituted phenyl C$_{1-5}$alkyl where the phenyl substitutents are halogen, C$_{1-5}$alkoxy, trihaloC$_{1-5}$alkyl or nitro, or R$_6$ is C$_{1-5}$alkoxycarbonyl, phenoxycarbonyl, substituted phenoxycarbonyl where the phenyl substitutents are halogen, C$_{1-5}$alkoxy, trihaloC$_{1-5}$alkyl or nitro; R$_7$ is C$_{1-10}$alkyl, substituted C$_{1-10}$alkyl where the substituents are halogen, trihaloC$_{1-5}$alkyl, C$_{1-5}$alkoxy, carboxy, C$_{1-5}$alkoxycarbonyl, amino, C$_{1-5}$alkylamino, diC$_{1-5}$alkylamino, diC$_{1-5}$alkylaminoC$_{1-5}$alkylamino, C$_{1-5}$alkylaminoC$_{1-5}$alkylamino or a heterocycle containing 4–8 ring atoms where one more of the ring atoms is nitrogen, oxygen or sulfur, where said heterocycle may be optionally substituted with C$_{1-5}$alkyl; or R$_7$ is phenyl, substituted phenyl (where the phenyl substitutents are one or more of C$_{1-5}$alkyl, halogen, C$_{1-5}$alkoxy, trihaloC$_{1-5}$alkyl or nitro), or R$_7$ is heteroaryl having 5–7 ring atoms where one or more atoms are nitrogen, oxygen or sulfur, fused heteroaryl where one or more 5–7 membered aromatic rings are fused to the heteroaryl, or R$_7$ is NR$_9$R$_{10}$ where R$_9$ and R$_{10}$ are independently selected from hydrogen and C$_{1-5}$alkyl or R$_9$ and R$_{10}$ may be taken together with the depicted nitrogen to form a heteroaryl ring of 5–7 ring members where one or more of the ring members is nitrogen, sulfur or oxygen where said heteroaryl ring may be optionally substituted with C$_{1-5}$alkyl;

TABLE Q

| | | Calcd | | | Found | | |
|---|---|---|---|---|---|---|---|
| Cpd | Empirical formula | C | H | N | C | H | N |
| 42 | C$_{28}$H$_{35}$N$_5$O$_3$ 2 C$_2$H$_2$O$_4$ 0.9 H$_2$O | 56.04 | 6.00 | 10.21 | 56.15 | 5.76 | 10.03 |
| 43 | C$_{26}$H$_{25}$N$_5$O$_3$ 1.2 C$_2$H$_2$O$_4$ | 60.53 | 4.90 | 12.43 | 60.28 | 5.08 | 12.23 |
| 44 | C$_{28}$H$_{32}$N$_4$O$_4$ C$_2$H$_2$O$_4$ 0.3 H$_2$O | 61.70 | 5.97 | 9.59 | 61.58 | 5.90 | 9.47 |
| 45 | C$_{29}$H$_{35}$N$_5$O$_3$ 1.75 C$_2$H$_2$O$_4$ | 59.22 | 5.89 | 10.62 | 59.49 | 6.18 | 10.34 |

$R_8$ is hydrogen, $C_{1-5}$alkyl, nitro, amino, and halogen; and pharmaceutically acceptable salts thereof.

2. The compound according to claim 1, N-hydroxy-N-(1-(1-(4-methoxyphenyl)-5-(4-methylphenyl)pyrazol-3-yl)-1-butyn-3-yl)urea.

3. The compound according to claim 1, N-hydroxy-N-(1-(5-(4-chlorophenyl)-1-(4-methoxyphenyl)pyrazol-3-yl)-1-propyn-3-yl)urea.

4. The compound according to claim 1, N-acetyl-N-(1-(1-(4-methoxyphenyl)-5-(4-methylphenyl)pyrazol-3-yl)-1-propyn-3-yl)hydroxylamine.

5. The compound according to claim 1, N-methoxycarbonyl-N-(1-(1-(4-methoxyphenyl)-5-(4-methylphenyl)pyrazol-3-yl)-1-propyn-3-yl)hydroxylamine.

6. The compound according to claim 1, N-isobutyryl-N-(1-(1-(4-methoxyphenyl)-5-(4-methylphenyl)pyrazol-3-yl)-1-butyn-3-yl)hydroxylamine.

7. The compound according to claim 1, N-trifluoroacetyl-N-(1-(1-(4-methoxyphenyl)-5-(4-methylphenyl)pyrazol-3-yl)-1-butyn-3-yl)hydroxylamine.

8. The compound according to claim 1, N-(furan-2-carbonyl)-N-(1-(1-(4-methoxyphenyl)-5(4-methylphenyl)pyrazol-3-yl)-1-butyn-3-yl)hydroxylamine.

9. The compound according to claim 1, N-acetyl-N-(1-(1-(4-methoxyphenyl)-5-(4-methylphenyl)pyrazol-3-yl)-1-pentyn-3-yl)hydroxylamine.

10. The compound according to claim 1, N-acetyl-N-(1-(5-(4-ethylphenyl)-1-(4-methoxyphenyl)pyrazol-3-yl)-1-butyn-3-yl)hydroxylamine.

11. The compound according to claim 1, N-isobutyryl-N-(1-(5-(4-ethylphenyl)-1-(4-methoxyphenyl)pyrazol-3-yl)-1-butyn-3-yl)hydroxylamine.

12. The compound according to claim 1, N-acetyl-N-(1-(5-(4-chlorophenyl)-1-(4-methoxyphenyl)pyrazol-3-yl)-1-butyn-3-yl)hydroxylamine.

13. The compound according to claim 1, N-methoxycarbony-N-(1-(5-(4-chlorophenyl)-1-(4-methoxyphenyl)pyrazol-3-yl)-1-butyn-3-yl)hydroxylamine.

14. The compound according to claim 1, N-(imidazol-1-yl)acetyl-N-(1-(1-(4-methoxyphenyl)-5(4-methylphenyl)pyrazol-3-yl)-1-butyn-3-yl)hydroxylamine.

15. A pharmaceutical composition for treating inflammatory related disorders comprising a compound of claim 1 in association with one or more pharmaceutically acceptable carriers.

16. A method of treating inflammatory related disorders in humans comprising administering to a human in need of such treatment an effective amount of a compound of claim 1.

* * * * *